United States Patent
Armstrong

(10) Patent No.: US 8,694,118 B2
(45) Date of Patent: Apr. 8, 2014

(54) VARIABLE OUTPUT RAMPING FOR AN IMPLANTABLE MEDICAL DEVICE

(75) Inventor: Randolph K. Armstrong, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 2057 days.

(21) Appl. No.: 11/262,465

(22) Filed: Oct. 28, 2005

(65) Prior Publication Data

US 2007/0097593 A1 May 3, 2007

(51) Int. Cl.
*A61N 1/00* (2006.01)

(52) U.S. Cl.
USPC .............................. 607/62; 607/73; 607/116

(58) Field of Classification Search
USPC ......................................... 607/2, 62, 73, 116
See application file for complete search history.

(56) References Cited

U.S. PATENT DOCUMENTS

| | | |
|---|---|---|
| 3,760,812 A | 9/1973 | Timm et al. |
| 4,305,402 A | 12/1981 | Katims |
| 4,338,945 A | 7/1982 | Kosugi et al. |
| 4,424,812 A | 1/1984 | Lesnick |
| 4,431,000 A | 2/1984 | Butler et al. |
| 4,459,989 A | 7/1984 | Borkan |
| 4,503,863 A | 3/1985 | Katims |
| 4,573,481 A | 3/1986 | Bullara |
| 4,590,946 A | 5/1986 | Loeb |
| 4,608,985 A | 9/1986 | Crish et al. |
| 4,612,934 A | 9/1986 | Borkan |
| 4,628,942 A | 12/1986 | Sweeney et al. |
| 4,649,936 A | 3/1987 | Ungar et al. |
| 4,702,254 A | 10/1987 | Zabara |
| 4,867,164 A | 9/1989 | Zabara |

(Continued)

FOREIGN PATENT DOCUMENTS

| | | |
|---|---|---|
| EP | 1070518 | 5/1984 |
| WO | 2004036377 A2 | 4/2004 |
| WO | 2004112894 A1 | 3/2005 |
| WO | 2005028026 A1 | 3/2005 |

OTHER PUBLICATIONS

Bachman, D.S, et al., "Effects of Vagal Volleys and Serotonin on Units of Cingulate Cortex in Monkeys," Brain Research, 130, (1977), pp. 253-269.

(Continued)

*Primary Examiner* — Mark W Bockelman
(74) *Attorney, Agent, or Firm* — Cyberonics, Inc.

(57) ABSTRACT

A method, system, and apparatus for providing a stimulation signal comprising a variable ramping portion using an implantable medical device (IMD). The first electrical comprises a first ramping portion. The first ramping portion comprises a first parameter selected from the group consisting of an amplitude, a rate of change of the amplitude, a time period of a rate of change of the amplitude, a pulse width, a rate of change of the pulse width, a time period of a rate of change of the pulse width, a frequency, a rate of change of the frequency, a time period of a rate of change of the frequency, and a duration of a time period of the ramping portion, the first parameter having a first value. The first electrical signal is applied to a target location of the patient's body. A second electrical signal comprising a second ramping portion is generated. The second ramping portion comprises the first parameter having a second value that is different from the first value. The second electrical signal is applied to a target location of the patient's body.

8 Claims, 14 Drawing Sheets

(56) References Cited

U.S. PATENT DOCUMENTS

| | | | |
|---|---|---|---|
| 4,920,979 A | 5/1990 | Bullara | |
| 4,949,721 A | 8/1990 | Toriu et al. | |
| 5,025,807 A | 6/1991 | Zabara | |
| 5,154,172 A | 10/1992 | Terry, Jr. et al. | |
| 5,188,104 A | 2/1993 | Wernicke et al. | |
| 5,205,285 A | 4/1993 | Baker, Jr. | |
| 5,215,086 A | 6/1993 | Terry, Jr. et al. | |
| 5,222,494 A | 6/1993 | Baker, Jr. | |
| 5,231,988 A | 8/1993 | Wernicke et al. | |
| 5,263,480 A | 11/1993 | Wernicke et al. | |
| 5,269,303 A | 12/1993 | Wernicke et al. | |
| 5,299,569 A | 4/1994 | Wernicke et al. | |
| 5,330,507 A | 7/1994 | Schwartz | |
| 5,330,515 A | 7/1994 | Rutecki et al. | |
| 5,334,221 A | 8/1994 | Bardy | |
| 5,354,320 A | 10/1994 | Schaldach et al. | |
| 5,411,531 A | 5/1995 | Hill et al. | |
| 5,411,540 A | 5/1995 | Edell et al. | |
| 5,423,872 A | 6/1995 | Cigaina | |
| 5,507,784 A | 4/1996 | Hill et al. | |
| 5,522,862 A * | 6/1996 | Testerman et al. | 607/42 |
| 5,522,865 A | 6/1996 | Schulman et al. | |
| 5,540,730 A | 7/1996 | Terry, Jr. et al. | |
| 5,540,734 A | 7/1996 | Zabara | |
| 5,571,150 A | 11/1996 | Wernicke et al. | |
| 5,601,617 A | 2/1997 | Loeb et al. | |
| 5,628,768 A * | 5/1997 | Lubbe | 607/46 |
| 5,645,570 A | 7/1997 | Corbucci | |
| 5,651,378 A | 7/1997 | Matheny et al. | |
| 5,658,318 A | 8/1997 | Stroetmann et al. | |
| 5,690,681 A | 11/1997 | Geddes et al. | |
| 5,690,688 A | 11/1997 | Noren et al. | |
| 5,700,282 A | 12/1997 | Zabara | |
| 5,702,429 A | 12/1997 | King | |
| 5,707,400 A | 1/1998 | Terry, Jr. et al. | |
| 5,755,750 A | 5/1998 | Petruska et al. | |
| 5,792,212 A | 8/1998 | Weijand | |
| 5,814,092 A | 9/1998 | King | |
| 5,836,994 A | 11/1998 | Bourgeois | |
| 5,861,014 A | 1/1999 | Familoni | |
| 5,916,239 A | 6/1999 | Geddes et al. | |
| 5,928,272 A | 7/1999 | Adkins et al. | |
| 6,002,966 A | 12/1999 | Loeb et al. | |
| 6,101,412 A | 8/2000 | Duhaylongsod | |
| 6,104,956 A | 8/2000 | Naritoku et al. | |
| 6,132,361 A | 10/2000 | Epstein et al. | |
| 6,141,590 A | 10/2000 | Renirie et al. | |
| 6,175,764 B1 | 1/2001 | Loeb et al. | |
| 6,219,580 B1 | 4/2001 | Faltys et al. | |
| 6,266,564 B1 | 7/2001 | Hill et al. | |
| 6,269,270 B1 | 7/2001 | Boveja | |
| 6,295,472 B1 | 9/2001 | Rubinstein et al. | |
| 6,308,102 B1 | 10/2001 | Sieracki et al. | |
| 6,339,725 B1 | 1/2002 | Naritoku et al. | |
| 6,341,236 B1 | 1/2002 | Osorio et al. | |
| 6,356,788 B2 | 3/2002 | Boveja | |
| 6,366,813 B1 | 4/2002 | DiLorenzo | |
| 6,374,140 B1 | 4/2002 | Rise | |
| 6,381,496 B1 | 4/2002 | Meadows et al. | |
| 6,381,499 B1 | 4/2002 | Taylor et al. | |
| 6,418,344 B1 | 7/2002 | Rezai et al. | |
| 6,425,852 B1 | 7/2002 | Epstein et al. | |
| 6,463,328 B1 | 10/2002 | John | |
| 6,473,644 B1 | 10/2002 | Terry, Jr. et al. | |
| 6,480,743 B1 | 11/2002 | Kirkpatrick et al. | |
| 6,487,446 B1 | 11/2002 | Hill et al. | |
| 6,522,928 B2 | 2/2003 | Whitehurst et al. | |
| 6,532,388 B1 | 3/2003 | Hill et al. | |
| 6,549,804 B1 | 4/2003 | Osorio et al. | |
| 6,556,868 B2 | 4/2003 | Naritoku et al. | |
| 6,564,102 B1 | 5/2003 | Boveja | |
| 6,579,280 B1 | 6/2003 | Kovach et al. | |
| 6,587,719 B1 | 7/2003 | Barrett et al. | |
| 6,587,724 B2 | 7/2003 | Mann | |
| 6,587,727 B2 | 7/2003 | Osorio et al. | |
| 6,591,138 B1 | 7/2003 | Fischell et al. | |
| 6,600,953 B2 | 7/2003 | Flesler et al. | |
| 6,609,025 B2 | 8/2003 | Barrett et al. | |
| 6,609,030 B1 | 8/2003 | Rezai et al. | |
| 6,611,715 B1 | 8/2003 | Boveja | |
| 6,615,081 B1 | 9/2003 | Boveja | |
| 6,622,038 B2 | 9/2003 | Barrett et al. | |
| 6,622,041 B2 | 9/2003 | Terry, Jr. et al. | |
| 6,622,047 B2 | 9/2003 | Barrett et al. | |
| 6,628,987 B1 | 9/2003 | Hill et al. | |
| 6,656,960 B2 | 12/2003 | Puskas | |
| 6,668,191 B1 | 12/2003 | Boveja | |
| 6,671,555 B2 | 12/2003 | Gielen et al. | |
| 6,671,556 B2 | 12/2003 | Osorio et al. | |
| 6,684,104 B2 | 1/2004 | Gordon et al. | |
| 6,684,105 B2 | 1/2004 | Cohen et al. | |
| 6,690,973 B2 | 2/2004 | Hill et al. | |
| 6,690,974 B2 | 2/2004 | Archer et al. | |
| 6,708,064 B2 | 3/2004 | Rezai | |
| 6,731,979 B2 | 5/2004 | MacDonald | |
| 6,731,986 B2 | 5/2004 | Mann | |
| 6,754,536 B2 | 6/2004 | Swoyer et al. | |
| 6,760,626 B1 | 7/2004 | Boveja | |
| 6,764,498 B2 | 7/2004 | Mische | |
| 6,768,969 B1 | 7/2004 | Nikitin et al. | |
| 6,775,573 B2 | 8/2004 | Schuler et al. | |
| 6,819,956 B2 | 11/2004 | DiLorenzo | |
| 6,826,428 B1 | 11/2004 | Chen et al. | |
| 6,832,114 B1 | 12/2004 | Whitehurst et al. | |
| 6,853,862 B1 | 2/2005 | Marchal et al. | |
| 6,885,888 B2 | 4/2005 | Rezai | |
| 6,895,278 B1 | 5/2005 | Gordon | |
| 6,920,357 B2 | 7/2005 | Osorio et al. | |
| 6,944,501 B1 | 9/2005 | Pless | |
| 6,961,618 B2 | 11/2005 | Osorio et al. | |
| 7,050,856 B2 | 5/2006 | Stypulkowski | |
| 7,054,686 B2 | 5/2006 | MacDonald | |
| 7,340,302 B1 * | 3/2008 | Falkenberg et al. | 607/9 |
| 2002/0099417 A1 | 7/2002 | Naritoku et al. | |
| 2003/0236558 A1 | 12/2003 | Whitehurst et al. | |
| 2004/0172094 A1 | 9/2004 | Cohen et al. | |
| 2004/0210270 A1 | 10/2004 | Erickson | |
| 2004/0210274 A1 | 10/2004 | Bauhahn et al. | |
| 2004/0249416 A1 | 12/2004 | Yun et al. | |
| 2005/0004621 A1 | 1/2005 | Boveja et al. | |
| 2005/0060007 A1 | 3/2005 | Goetz | |
| 2005/0060008 A1 | 3/2005 | Goetz | |
| 2005/0060009 A1 | 3/2005 | Goetz | |
| 2005/0060010 A1 | 3/2005 | Goetz | |
| 2005/0065562 A1 | 3/2005 | Rezai | |
| 2005/0065573 A1 | 3/2005 | Rezai | |
| 2005/0065575 A1 | 3/2005 | Dobak | |
| 2005/0075691 A1 | 4/2005 | Phillips et al. | |
| 2005/0119703 A1 | 6/2005 | DiLorenzo | |
| 2005/0131485 A1 | 6/2005 | Knudson et al. | |
| 2005/0131506 A1 | 6/2005 | Rezai et al. | |
| 2005/0154425 A1 | 7/2005 | Boveja et al. | |
| 2005/0192644 A1 | 9/2005 | Boveja et al. | |
| 2005/0283200 A1 | 12/2005 | Rezai et al. | |
| 2006/0009815 A1 | 1/2006 | Boveja | |
| 2006/0079936 A1 | 4/2006 | Boveja | |
| 2006/0095081 A1 | 5/2006 | Zhou et al. | |

OTHER PUBLICATIONS

Boon, Paul et al., "Programmed and Magnet-Induced Vagus Nerve Stimulation for Refractory Epilepsy," Journal of Clinical Neurophysiology, vol. 18, No. 5, 2001, pp. 402-407.

Degiorgio, Christopher M. et al., "Vagus Nerve Stimulation: Analysis of Device Parameters in 154 Patients During the Long-Term XE5 Study," Epilepsia, vol. 42, No. 8, 2001, pp. 1017-1020.

Fanselow, Erika E. et al., "Reduction of Pentylenetetrazole-Induced Seizure Activity in Awake Rats by Seizure-Triggered Trigeminal Nerve Stimulation," The Journal of Neuroscience, vol. 20, No. 21, Nov. 1, 2000, pp. 8160-8168.

Hallowitz, R.A., et al., "Effects of Vagal Volleys on Units of Intralaminar and Juxtalaminar Thalamic Nuclei in Monkeys," Brain Research, 130, (1977), pp. 271-286.

(56) References Cited

OTHER PUBLICATIONS

Harry, Jason D. et al., "Balancing Act," IEEE Spectrum, Apr. 2005, pp. 37-41.

Henry, Thomas R. et al., "Brain Blood Flow Alterations Induced by Therapeutic Vagus Nerve Stimulation in Partial Epilepsy: I. Acute Effects At High and Low Levels of Stimulation," Epilepsia, vol. 39, No. 9, 1998, pp. 983-990.

Lockard, J.S., et al., "Feasibility and Safety of Vagal Stimulation in Monkey Model," Epilepsia, 31, (Suppl.2), (1990), pp. S20-S26.

McClintock, Peter "Can Noise Actually Boost Brain Power?," Physics World, Physics in Action, Jul. 2002, pp. 20-21.

Mori, Toshio et al., "Noise-Induced Entrainment and Stochastic Resonance in Human Brain Waves," Physical Review Letters, vol. 88, No. 21, May 27, 2002, pp. 218101-1 to 218101-4.

Schacter, Steven C., et al., "Vagus Nerve Stimulation," Epilepsia, vol. 39, No. 7, 1998, pp. 677-686.

Terry, R.S., et al., "The Implantable Neurocybernetic Prosthesis System," Pacing and Clinical Electrophysiology, vol. 14, No. 1, (Jan. 1991), pp. 86-93.

\* cited by examiner

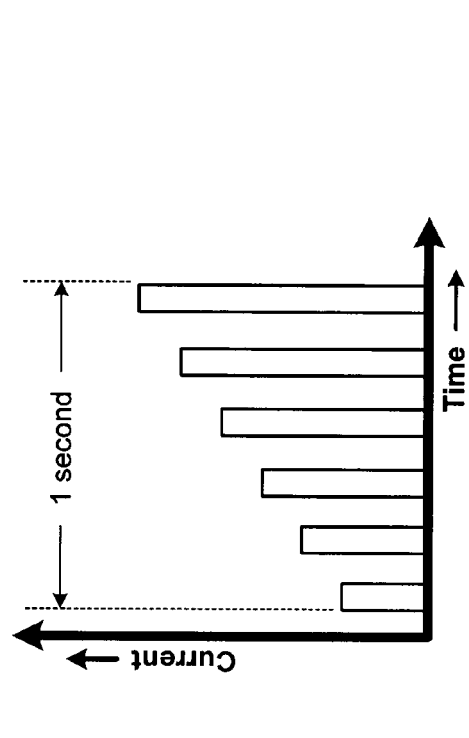
FIGURE 6B
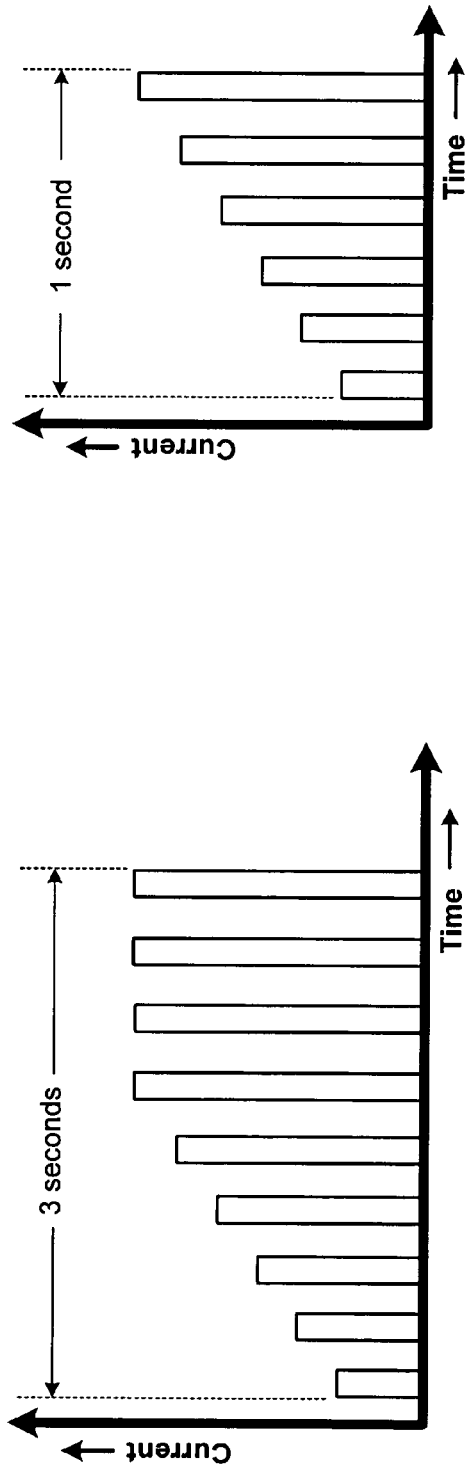
FIGURE 6A
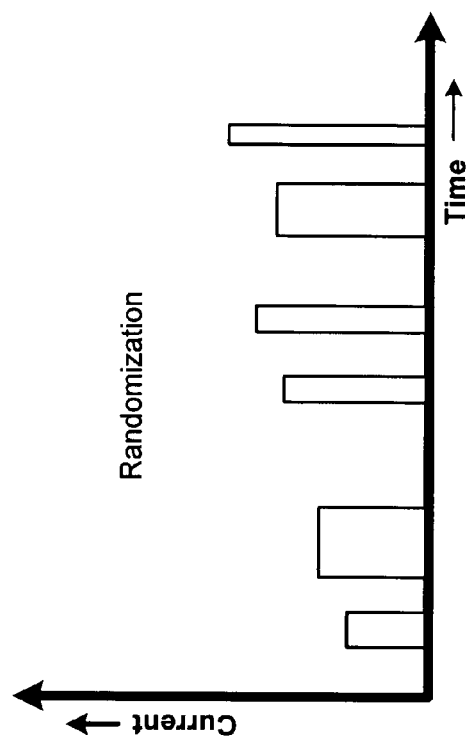
FIGURE 7C
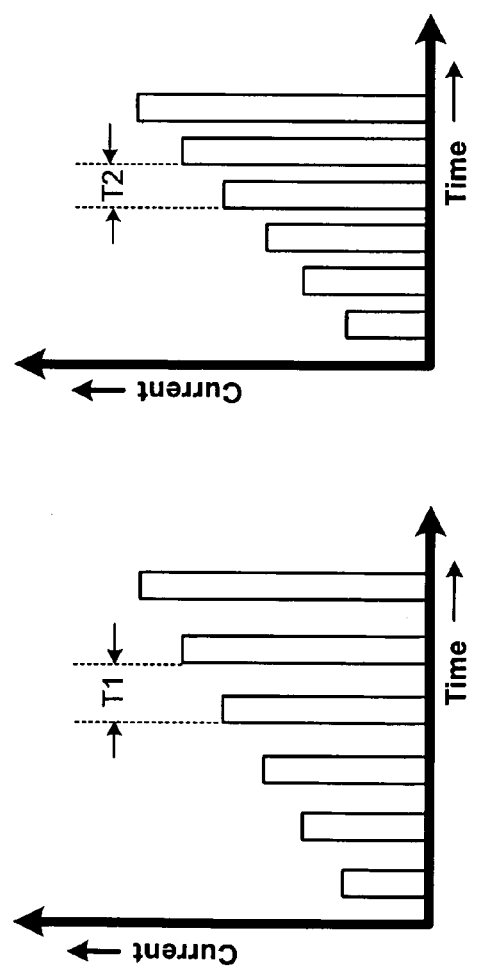
FIGURE 7B
FIGURE 7A

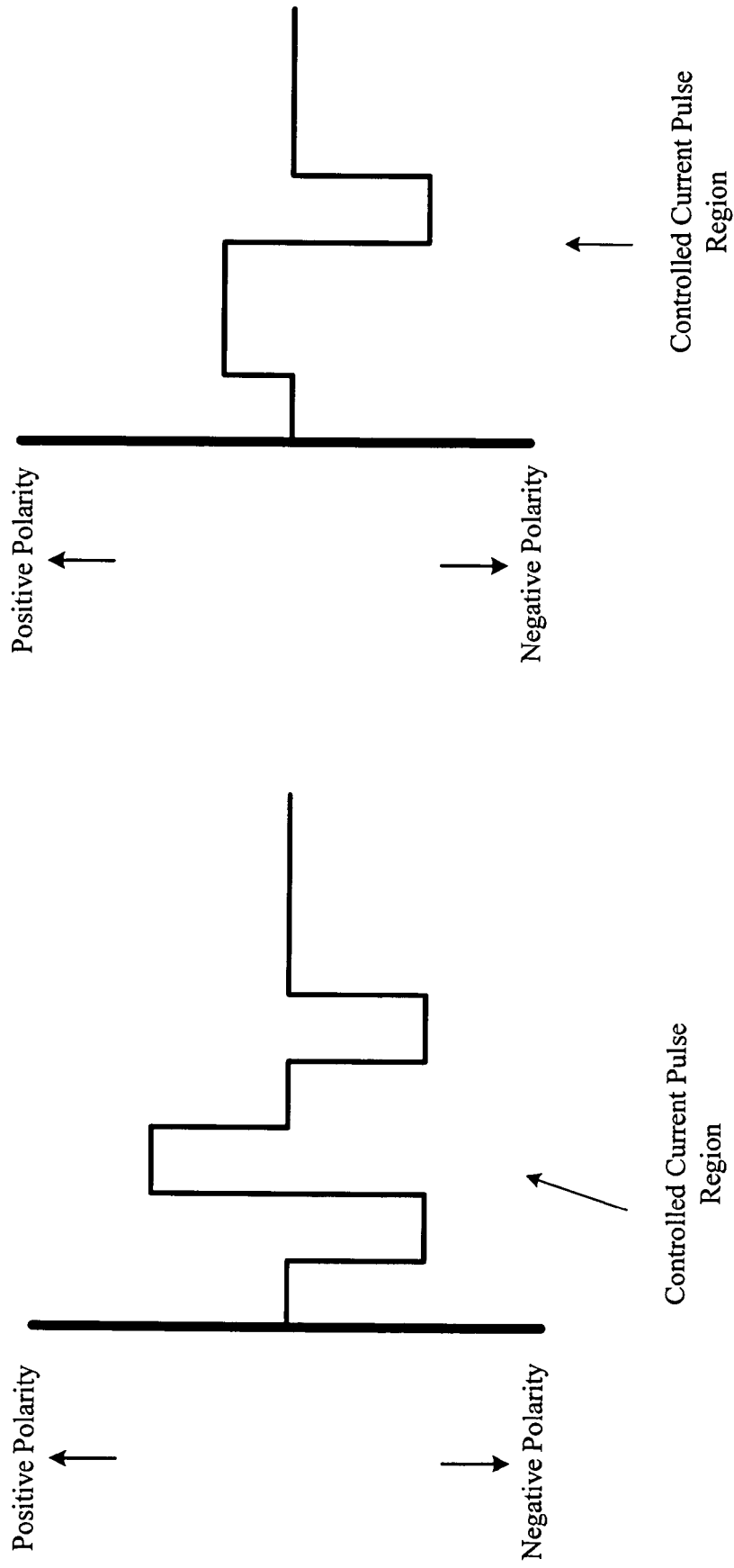

VARIABLE OUTPUT RAMPING FOR AN IMPLANTABLE MEDICAL DEVICE

BACKGROUND OF THE INVENTION

1. Field of the Invention

This invention relates generally to implantable medical devices, and, more particularly, to methods, apparatus, and systems for providing a variable output ramping signal associated with delivering a therapeutic electrical signal to a target portion of a patient's body.

2. Description of the Related Art

There have been many improvements over the last several decades in medical treatments for disorders of the nervous system, such as epilepsy and other motor disorders, and abnormal neural discharge disorders. One of the more recently available treatments involves the application of an electrical signal to reduce various symptoms or effects caused by such neural disorders. For example, electrical signals have been successfully applied to target locations in the human body to provide various benefits, including reducing occurrences of seizures and/or improving or ameliorating other conditions. A particular example of such a treatment regimen involves applying an electrical signal to the vagus nerve of the human body to reduce or eliminate epileptic seizures, as described in U.S. Pat. No. 4,702,254 to Dr. Jacob Zabara, which is hereby incorporated in its entirety by reference in this specification. Electrical stimulation of the vagus nerve (hereinafter referred to as vagus nerve stimulation therapy or VNS) may be provided by implanting an electrical device underneath the skin of a patient and performing a detection and electrical stimulation process. Alternatively, the system may operate without a detection system once the patient has been diagnosed with epilepsy, and may periodically apply a series of electrical pulses to the vagus (or other cranial) nerve intermittently throughout the day, or over another predetermined time interval.

When delivering therapeutic electrical signals to neural structures in a patient's body, there may be a concern that a sudden burst of energy provided by the stimulation signal may not be tolerated well by the patient's body. For example, a sudden initiation of an electrical signal may cause an undesired reaction or side effect (e.g., pain). In addition to undesired side effects, a sudden burst of energy resulting from an electrical signal may not produce the intended therapeutic effect. Without being bound by theory, the targeted neural structure may not react properly (e.g., improper processing of the stimulation signal) when a sudden electrical signal is applied. Further, the signal may cause excessive neural conditioning, wherein the target may become conditioned to accept the electrical signal and as a result may not react as expected. This may reduce the efficacy of the therapy being delivered to the patient's body.

In an attempt to alleviate such problems, designers have provided for a ramping time period immediately before and/or after the delivery of the therapeutic electrical signal, in which the electrical signal applied to the target neural structure is gradually increased prior to delivery of the therapeutic dosage of the electrical signal ("ramp-up") or decreased after its delivery ("ramp-down"). State-of-the-art neurostimulators utilize the ramp-up or ramp-down periods to provide a gradual transition from the delivery of no electrical signal to the delivery of the full therapeutic dosage of the electrical signal (ramp-up) and/or from delivery of the full therapeutic dosage to the delivery of no signal (ramp-down). The ramp-up and ramp-down periods are thus used as a buffer to prepare the target neural structure to receive a full dosage electrical signal. The ramp-up and ramp-down periods provide a transition for the human body to enter or exit both a state of no stimulation and a stimulation state.

There are various limitations associated with state-of-the-art ramping-up and ramping-down methods. Most significantly, the ramp-up and ramp-down process may increase a likelihood of neural conditioning, in which the target structure becomes conditioned to accommodate the therapeutic electrical signal, with the result that therapeutic efficacy of the electrical signal may be diminished. Therefore, the state-of-the-art ramping-up and the ramping-down processes may promote significant neural conditioning that may lead to a reduction in the efficacy of stimulation treatment.

Generally, state-of-the-art ramp-up and ramp-down signal-portions call for ramping-up or ramping-down of the current amplitude of the electrical signal over a fixed duration (e.g., approximately 2 seconds), with fixed step sizes (e.g., 0.25 milliamps per step). This constant ramp-up and ramp-down signal may cause the target neural structure to become conditioned to receiving such constant, steady signal patterns, with a consequent reduction in therapeutic efficacy.

The present invention is directed to overcoming, or at least reducing, the effects of one or more of the problems set forth above.

SUMMARY OF THE INVENTION

In one aspect, the present invention comprises a method for providing a stimulation signal comprising a variable ramping portion using an implantable medical device (IMD). A first electrical signal is generated. The first electrical comprises a first ramping portion. The first ramping portion comprises a first parameter selected from the group consisting of an amplitude, a rate of change of the amplitude, a time period of a rate of change of the amplitude, a pulse width, a rate of change of the pulse width, a time period of a rate of change of the pulse width, a frequency, a rate of change of the frequency, a time period of a rate of change of the frequency, and a duration of a time period of the ramping portion, the first parameter having a first value. The first electrical signal is applied to a target location of the patient's body. A second electrical signal comprising a second ramping portion is generated. The second ramping portion comprises the first parameter having a second value that is different from the first value. The second electrical signal is applied to a target location of the patient's body.

In another aspect, the present invention comprises a method for providing a stimulation signal comprising a variable ramping portions using an implantable medical device. A first value of a first parameter of a first ramping portion associated with a first electrical signal is determined. The parameter being selected from the group consisting of an amplitude, a rate of change of the amplitude, a time period of a rate of change of the amplitude, a pulse width, a rate of change of the pulse width, a time period of a rate of change of the pulse width, a frequency, a rate of change of the frequency, a time period of a rate of change of the frequency, and a duration of a time period of the ramping portion. The first electrical signal is delivered to a target location of the patient's body. The first value is modified to provide a second value for the first parameter. A second electrical signal comprising a second ramping portion having the second value of the first parameter is generated. The second electrical signal is applied to a target location of the patient's body.

In yet another aspect, the present invention comprises a method for providing a stimulation signal comprising a variable ramping portion using an implantable medical device. A characteristic of a ramping portion of a stimulation signal provided by the IMD is determined. The characteristic being selected from the group consisting of an amplitude, a rate of change of the amplitude, a time period of a rate of change of the amplitude, a pulse width, a rate of change of the pulse width, a time period of a rate of change of the pulse width, a frequency, a rate of change of the frequency, a time period of a rate of change of the frequency, and a duration of a time period of the ramping portion. The stimulation signal is provided based upon the characteristic of the ramping portion.

In another aspect, the present invention comprises an implantable medical device for providing a stimulation signal comprising a variable ramping portion. The IMD includes a stimulation unit adapted to provide a first electrical signal comprising a first ramping portion. The first ramping portion comprises a characteristic being selected from the group consisting of an amplitude, a rate of change of the amplitude, a time period of a rate of change of the amplitude, a pulse width, a rate of change of the pulse width, a time period of a rate of change of the pulse width, a frequency, a rate of change of the frequency, a time period of a rate of change of the frequency, and a duration of a time period of the first ramping portion. The IMD also comprises a controller operatively coupled to the stimulation unit. The controller being adapted to control a first value of the characteristic of the first ramping portion.

BRIEF DESCRIPTION OF THE DRAWINGS

The invention may be understood by reference to the following description taken in conjunction with the accompanying drawings, in which like reference numerals identify like elements, and in which:

FIGS. 6A-6B illustrate a modification of the duration of a ramp-up signal, in accordance with one illustrative embodiment of the present invention;

FIGS. 7A-7B illustrate a frequency modification of a ramp-up signal, in accordance with one illustrative embodiment of the present invention;

FIG. 7C illustrates a randomized implementation of a ramp-up signal, in accordance with one illustrative embodiment of the present invention;

FIGS. 8A-8F illustrate various illustrative depictions of multi-phase signals, in accordance with one illustrative embodiment of the present invention;

Figure 1A:
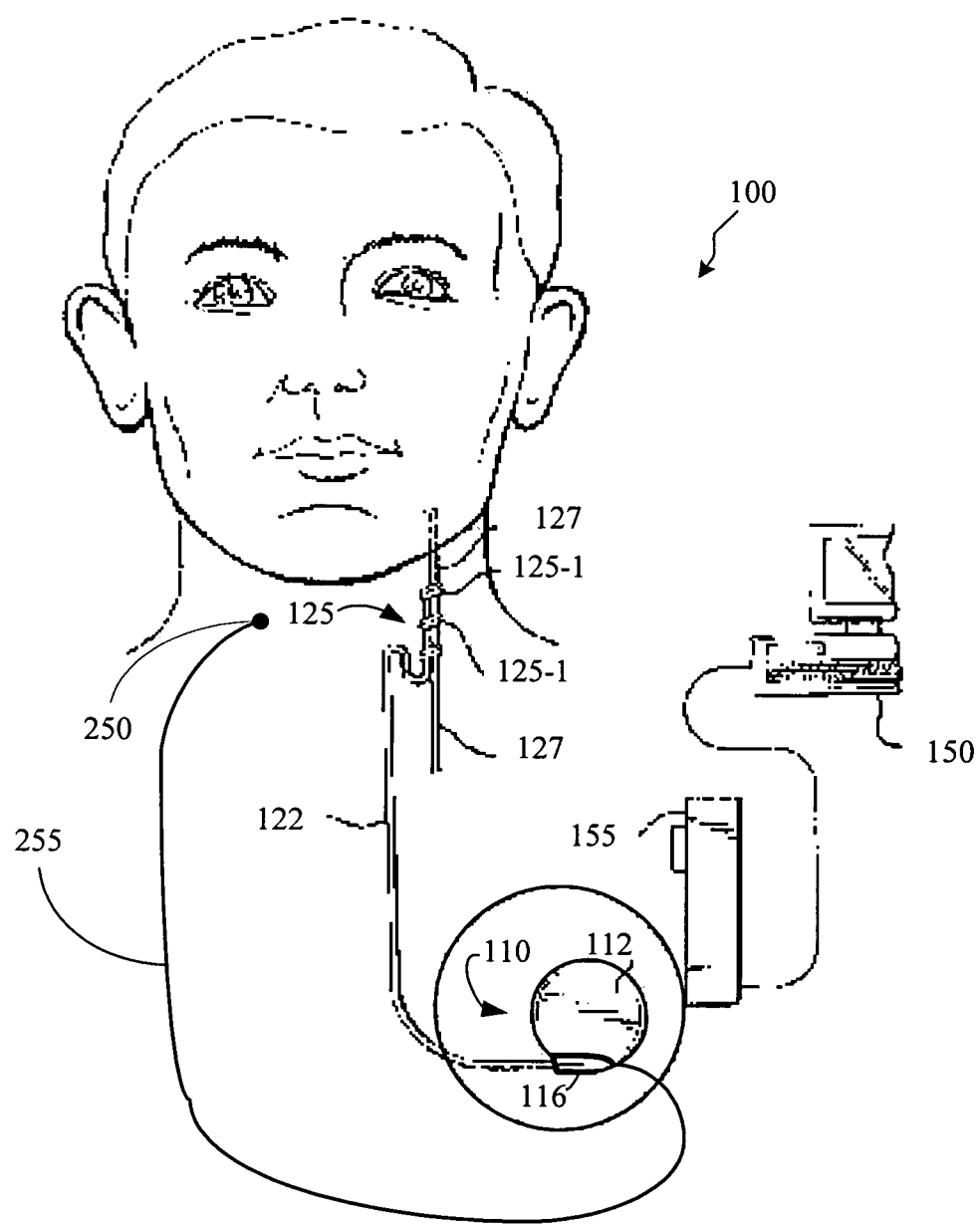
FIGS. 1A-1D provide stylized diagrams of an implantable medical device implanted into a patient's body for providing stimulation to a portion of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Embodiments of the present invention provide for a method, apparatus, and an implantable medical system for controlling a stimulation signal to provide a variable ramping portion of the stimulation signal. The ramping portion may relate to a ramping-up portion immediately preceding the therapeutic portion of the stimulation signal. The ramping portion may also relate to a ramping-down portion of immediately following the therapeutic portion of the stimulation. Although not so limited, a system capable of implementing embodiments of the present invention is described below. FIGS. 1A-1D illustrate an implantable medical system 100 that is capable of entering a safe-mode operation in response to a presence of a coupled signal/energy experienced by a component of the system 100. The safe-mode operation may involve adjusting an impedance associated with the portion of the implantable medical system 100 that is experiencing the presence of the coupled signal/energy. The system 100 is also capable of detecting when the coupled signal/energy has been removed or substantially reduced, and returning to a normal operating mode.

FIGS. 1A-1D depict a stylized implantable medical system 100 for implementing one or more embodiments of the present invention. FIGS. 1A-1D illustrate a signal generator 110 having a main body 112 comprising a case, or shell 121, with an electrical connector 116 in a header 114 (FIG. 1C) for connecting to leads 122. The signal generator 110 is implanted in the patient's chest in a pocket or cavity formed by the implanting surgeon just below the skin (indicated by a dotted line 145, FIG. 1B), similar to the implantation procedure for a pacemaker pulse generator.

A stimulating electrode assembly 125, preferably comprising an electrode pair, is conductively connected to the distal end of an insulated electrically conductive lead assembly 122, which preferably comprises a pair of lead wires (one wire for each electrode of an electrode pair). Lead assembly 122 is attached at its proximal end to the electrical connector 116 on header 114. The electrode assembly 125 is surgically coupled to the patient's tissue, e.g., a vagus nerve 127 in the patient's neck. The present invention is suitable for use in implantable medical devices connected to any body tissue, e.g., a pacemaker coupled to heart tissue. The electrode assembly 125 preferably comprises a bipolar stimulating electrode pair (FIG. 1D), such as the electrode pair described in U.S. Pat. No. 4,573,481 issued Mar. 4, 1986 to Bullara. Persons of skill in the art will appreciate that many electrode designs could be used in the present invention. For embodiments of the present invention involving vagus nerve stimulation, two electrodes are preferably wrapped about the vagus nerve, and the electrode assembly 125 is preferably secured to the nerve 127 by a spiral anchoring tether 128 (FIG. 1D) such as that disclosed in U.S. Pat. No. 4,979,511 issued Dec. 25, 1990 to Reese S. Terry, Jr., and assigned to the same assignee as the instant application. Lead assembly 122 is secured, while retaining the ability to flex with movement of the chest and neck, by a suture connection 130 to nearby tissue.

In one embodiment of the present invention involving nerve stimulation, the open helical design of the electrode assembly 125 (described in detail in the above-cited Bullara patent), which is self-sizing and flexible, minimizes mechanical trauma to the nerve and allows body fluid interchange with the nerve. The electrode assembly 125 preferably conforms to the shape of the nerve, providing a low stimulation threshold by allowing a large stimulation contact area with the nerve. Structurally, the electrode assembly 125 comprises two electrode ribbons (not shown) of a conductive material such as platinum, iridium, platinum-iridium alloys, and/or oxides of the foregoing. The electrode ribbons are individually bonded to an inside surface of an elastomeric body portion of the two spiral electrodes 125-1 and 125-2 (FIG. 1D), which may comprise two spiral loops of a three-loop helical assembly. The elastomeric body portion of each loop preferably comprises silicone rubber, and the third loop 128 (which typically has no electrode) acts as the anchoring tether 128 for the electrode assembly 125.

The lead assembly 122 may comprise two distinct lead wires or a coaxial cable whose two conductive elements are respectively coupled to one of the conductive electrode ribbons 125-1 and 125-2. One suitable method of coupling the lead wires or cable to the electrodes comprises a spacer assembly such as that disclosed in U.S. Pat. No. 5,531,778 (Maschino), although other known coupling techniques may be used.

Figure 1B:
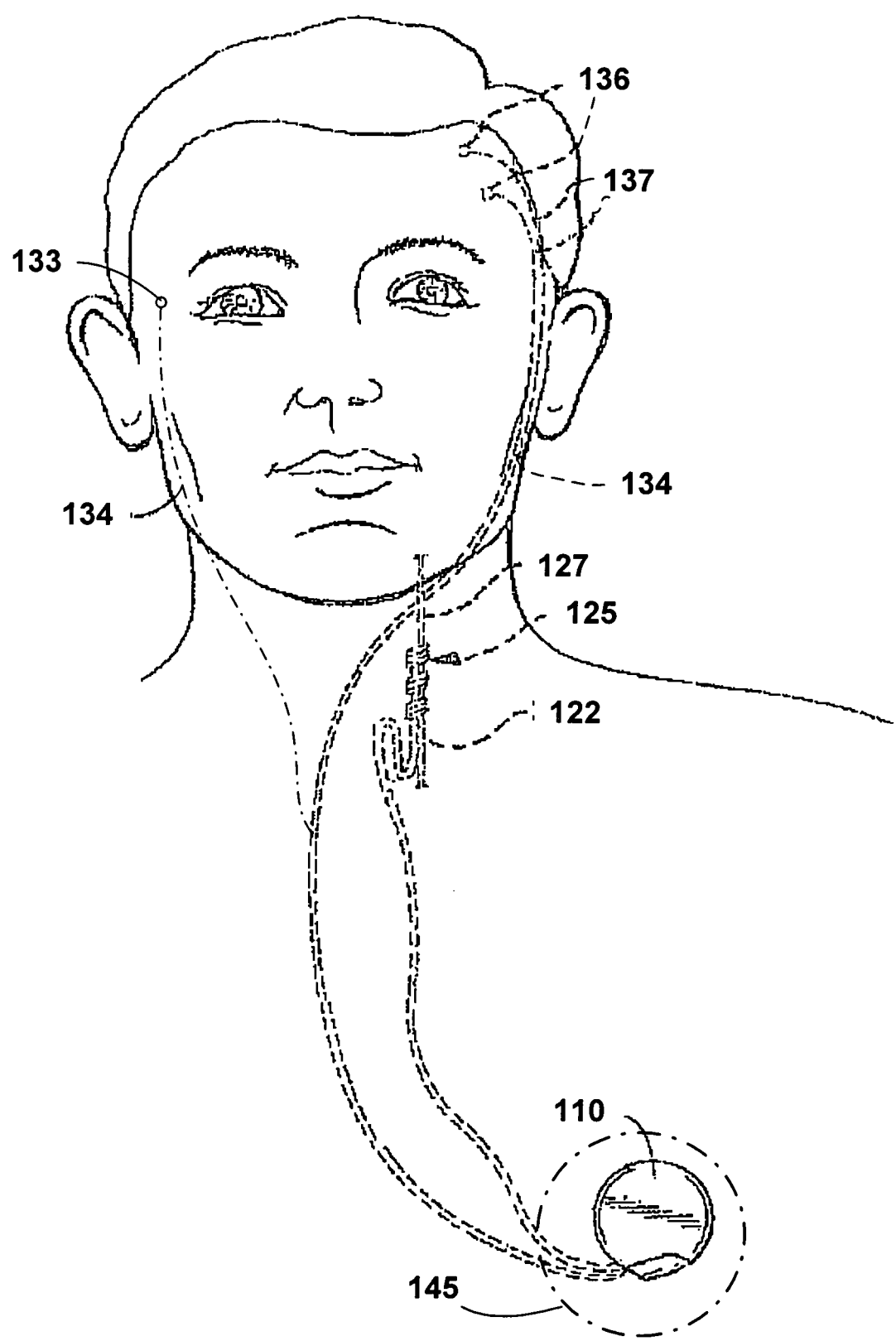
Figure 1C:
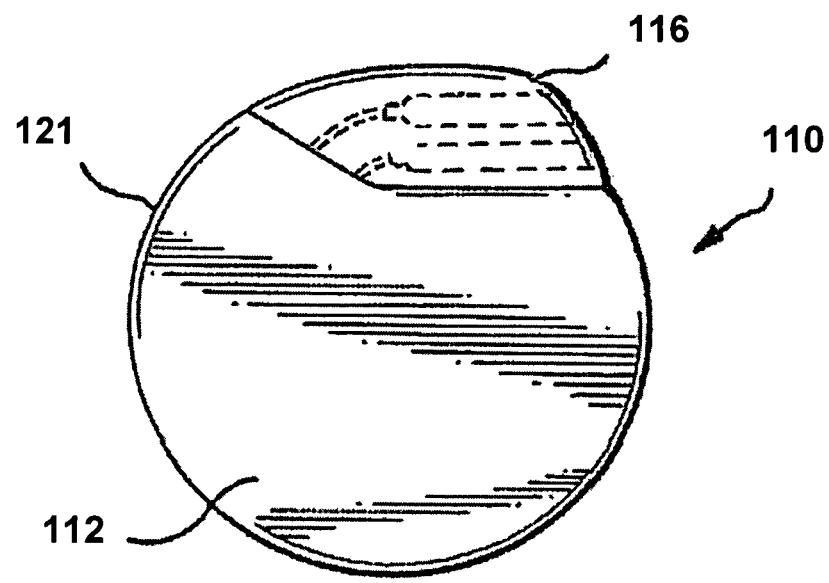

In certain embodiments of the present invention, sensing elements may be used to provide data to the implantable medical system 100 concerning one or more body parameters. Although exemplary sensors are disclosed herein, persons of skill in the art will appreciate that the present invention is not limited to particular embodiments. Referring to FIG. 1B, eye movement sensing electrodes 133 may be implanted at or near an outer periphery of each eye socket in a suitable location to sense muscle movement or actual eye movement. The electrodes 133 may be electrically connected to leads 134 implanted via a catheter or other suitable means (not shown) and extending along the jawline through the neck and chest tissue to the signal generator 110. When included in systems of the present invention, the sensing electrodes 133 may be utilized for detecting rapid eye movement (REM) in a pattern indicative of a disorder to be treated, as described in greater detail below.

Alternatively or additionally, EEG sensing electrodes 136 may optionally be implanted in spaced apart relation through the skull, and connected to leads 137 implanted and extending along the scalp and temple and then to the signal generator 110 in the same manner as described above for the eye movement electrode leads. Electrodes 133 and 136, or other types of sensors, may be used in some embodiments of the invention to trigger administration of the electrical stimulation therapy to the vagus nerve 127 via electrode assembly 125. Use of such sensed body signals to trigger or initiate stimulation therapy is hereinafter referred to as a "feedback" or "active" stimulation. Other embodiments of the present invention utilize a stimulation therapy delivered according to a programmed on/off duty cycle without the use of sensors to trigger therapy delivery. This type of delivery may be referred to as "passive," "non-feedback," or prophylactic stimulation. Both active and passive stimulation may be combined or delivered by a single IMD 300 according to the present invention. Either or both modes may be appropriate to treat the particular disorder diagnosed in the case of a specific patient under observation. The therapeutic electrical signal may be a continuous or pulsed signal; either type of signal may be applied periodically or intermittently to the vagus nerve.

The signal generator 110 may be programmed with an external computer 150 (FIG. 1A) using programming software of the type copyrighted by the assignee of the instant application with the Register of Copyrights, Library of Congress, or other suitable software based on the description herein, and a programming wand 155 may be used to facilitate radio frequency (RF) communication between the computer 150 and the signal generator 110. The wand 155 and software permit noninvasive communication with the generator 110 after the latter is implanted. The wand 155 is preferably powered by internal batteries, and provided with a "power on" light to indicate sufficient power for communication. Another indicator light may be provided to show that data transmission is occurring between the wand and the generator.

A wide variety of stimulation therapies may be provided in implantable medical systems 100 of the present invention. Different types of nerve fibers (e.g., A, B, and C fibers being different fibers targeted for stimulation) respond differently to stimulation from electrical signals. More specifically, the different types of nerve fibers have different conduction velocities and stimulation thresholds and, therefore, differ in their responsiveness to stimulation. Certain pulses of an electrical stimulation signal, for example, may be below the stimulation threshold for a particular fiber and, therefore, may generate no action potential in the fiber. Thus, smaller or narrower pulses may be used to avoid stimulation of certain nerve fibers (such as C fibers) and target other nerve fibers (such as A and/or B fibers, which generally have lower stimulation thresholds and higher conduction velocities than C fibers). Additionally, techniques such as pre-polarization may be employed wherein particular nerve regions may be polarized before a more robust stimulation is delivered, which may better accommodate particular electrode materials. Furthermore, opposing polarity phases separated by a zero current phase may be used to excite particular axons or postpone nerve fatigue during long term stimulation.

Embodiments of the present invention provide for an adjustable ramping-up and/or ramping-down functions for delivering a stimulation signal. The ramp-up portion of the stimulation signal (i.e., the portion immediately preceding the therapeutic portion of the stimulation signal), as well as the ramp-down portion (i.e., the portion immediately following the therapeutic portion of the stimulation signal), may be adjusted and/or varied. These variations may be based on various factors and may be implemented to enhance the therapeutic effects of the stimulation signal.

Embodiments of the present invention provide for a programmable and/or controllable ramping-up portion and/or a ramping-down portion of the stimulation signal. The programmable/controllable ramping portion of the stimulation signal may be adjusted in response to various factors, such as external commands, pre-programmed timing, efficacy feedback data, etc. Various components or characteristics of the signal may be adjusted during the ramp-up and/or ramp-down portions. For example, characteristics of the ramp-up and/or ramp-down signals may include an amplitude, a rate of change of the amplitude, a time period of a rate of change of the amplitude, a pulse width, a rate of change of the pulse width, a time period of a rate of change of the pulse width, a frequency, a rate of change of the frequency, a time period of a rate of change of the frequency, and/or a duration of a time period of the ramp-up and/or ramp-down portions. These characteristics may be modified automatically or manually. In an alternative embodiment, various characteristics of the ramping-up and/or ramping-down portions may be randomly modified. In addition, the ramping-up and/or ramping-down portions of the stimulation signal may employ a multi-phasic signal that may provide a plurality of phases in which various signal-characteristics may be modified. Utilizing embodiments of the present invention, an increase in the effectiveness of the stimulation signal may be realized.

Figure 2:
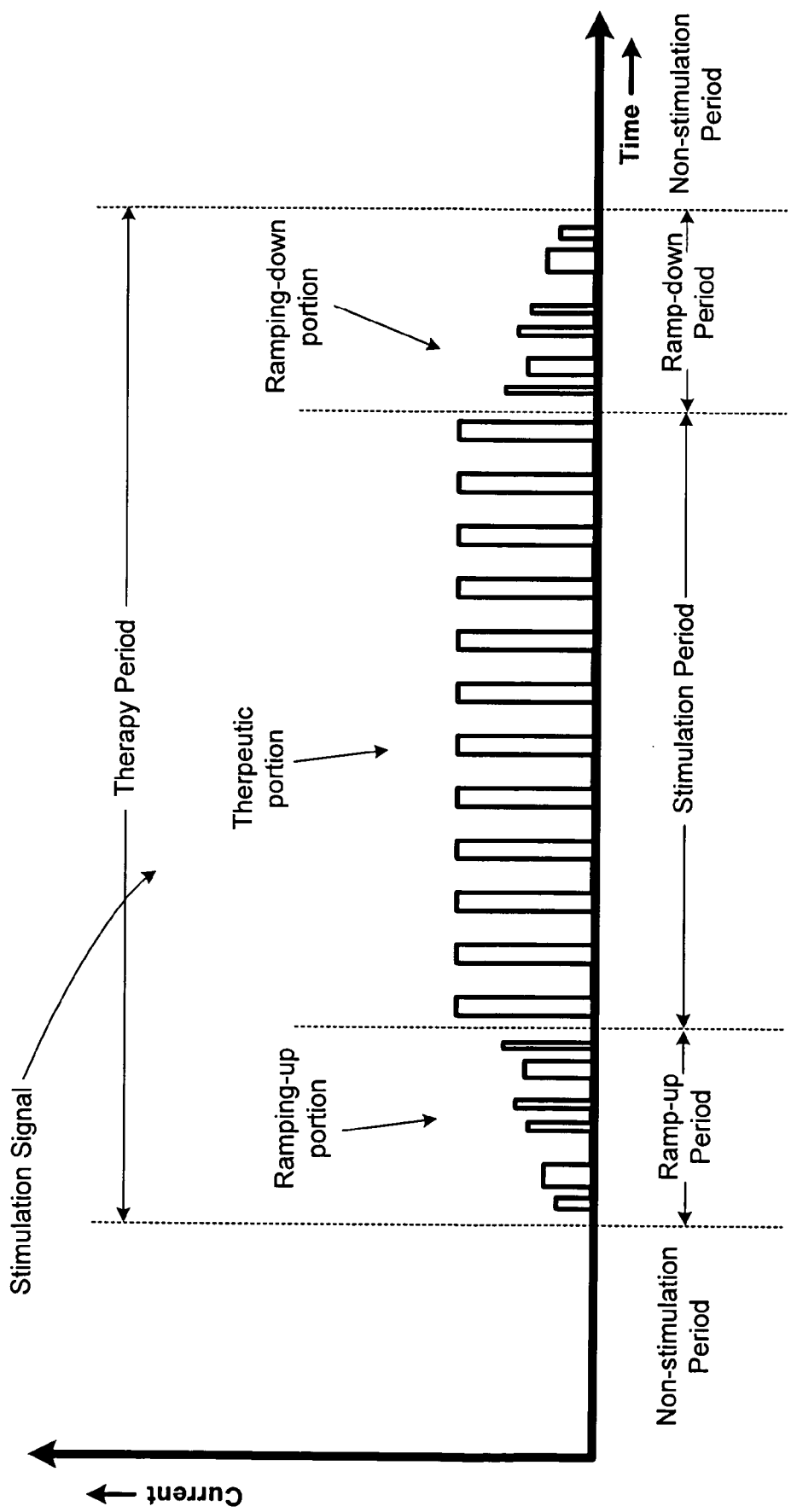
FIG. 2 provides a stylized depiction of a ramp-up period, a stimulation period, and a ramp-down period, in accordance with one illustrative embodiment of the present invention.

Turning now to FIG. 2, a stylized illustration of a stimulation signal that comprises a stimulation period, a ramp-up period, and a ramp-down period, is depicted. While substantially always remaining operational, the implantable medical device may enter substantial non-stimulation periods where no significant stimulation is provided to a patient. This non-stimulation period may be interrupted by a therapy period, in which a stimulation signal is provided. By way of example only, the non-stimulation period may be of a duration of approximately two minutes, where the therapy period may be of a duration of approximately 30 seconds.

In one embodiment, the therapy period comprises three subsections. The therapy period may comprise a ramp-up period, during which a signal portion is provided in a generally upward ramping format to prepare a targeted portion of the body (e.g., targeted portion of a vagus nerve) for receiving a therapy signal. The ramping-up signal in the ramp-up period may cause the targeted portion of the body to provide increased reaction to the stimulation signal. In other words, the ramping-up signal provides for improving the efficacy of the therapy provided by the stimulation signal. The ramp-up period is followed by a stimulation period in which therapeutic stimulation is delivered to a portion of the patient's body. The signal response during the stimulation period may reflect a constant signal depicted in FIG. 2, and/or may include similar type characteristics as the ramping portions.

The stimulation signal period may then be followed by the ramp-down period. The ramp-down period comprises a generally ramping-down signal portion that provides for preparing the targeted portion of the patient's body that receives the stimulation signal to enter a non-stimulation period. The ramping-up signal and the ramping-down signal illustrated in FIG. 2, may be programmed and/or otherwise controlled to provide for increased efficacy of the therapy provided by the stimulation signal. Various characteristics of the ramping-up and/or ramping-down signals may be modified. For example, the characteristics may include, but are not limited to, an amplitude, a rate of change of the amplitude, a time period of a rate of change of the amplitude, a pulse width, a rate of change of the pulse width, a time period of a rate of change of the pulse width, a frequency, a rate of change of the frequency, a time period of a rate of change of the frequency, and/or a duration of a time period of the ramp-up and/or ramp-down portions. Further, a multi-phasic signal may be provided during the ramp-up and ramp-down periods.

Still further, a randomized modification of the characteristics of the ramp-up and the ramp-down signals may be implemented. The randomized signal may provide for an implementation of signals in which various characteristics described above may be randomly altered. The randomized ramping portion of the stimulation signal may provide for a reduction in neural conditioning. This may provide for an increased efficacy of the therapy provided by the stimulation signal. The length of the ramp-up period and the ramp-down period may also be modified. When modifying the duration of the ramp-up and/or the ramp-down periods, encroachment into the non-stimulation period and/or encroachment into the stimulation period may be made.

Figure 1D:
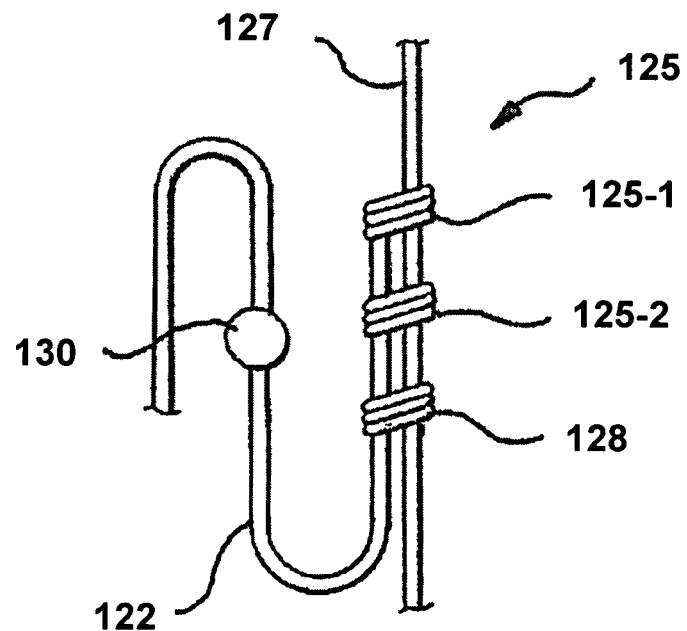
Figure 3:
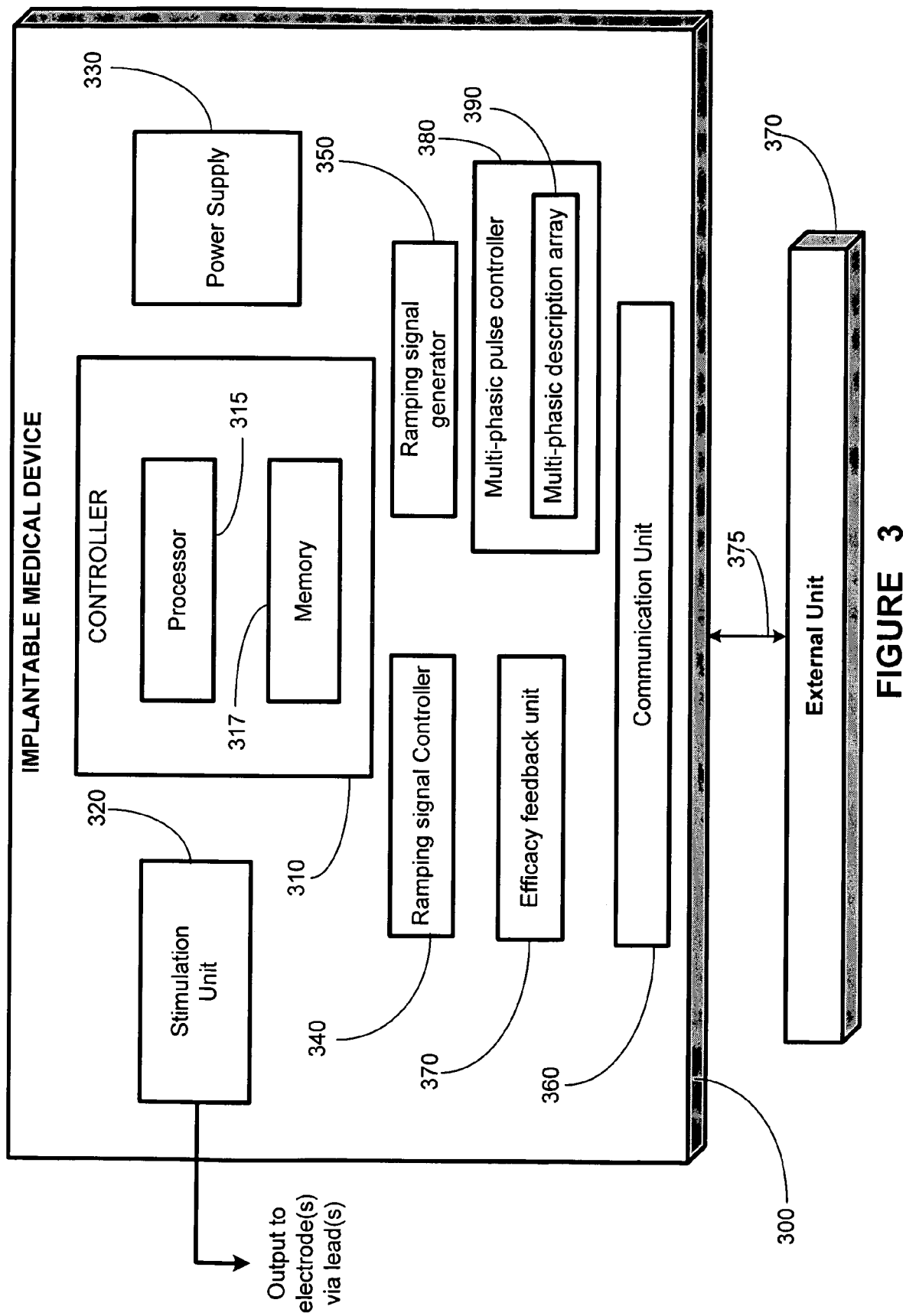
FIG. 3 provides a block diagram depiction of an implantable medical device, in accordance with one illustrative embodiment of the present invention.

Turning now to FIG. 3, a block diagram depiction of an implantable medical device (IMD) in accordance with one illustrative embodiment of the present invention is provided. The IMD 300 may be used for stimulation to treat various disorders, such as epilepsy, depression, bulimia, heart rhythm disorders, etc. The IMD 300 may be coupled to various leads, e.g., 122, 134, 137 (FIGS. 1A, 1B, 1D). Stimulation signals used for therapy may be transmitted from the IMD 300 to target areas of the patient's body, specifically to various electrodes associated with the leads 122. Stimulation signals from the IMD 300 may be transmitted via the leads 122 to stimulation electrodes associated with the electrode assembly 125 (FIG. 1A). Further, signals from sensor electrodes, e.g., 133, 136 (FIG. 1B) associated with corresponding leads, e.g., 134, 137, may also traverse the leads back to the IMD 300.

The IMD 300 may comprise a controller 310 capable of controlling various aspects of the operation of the IMD 300. The controller 310 is capable of receiving internal data and/or external data and generating and delivering a stimulation signal to target tissues of the patient's body. For example, the controller 310 may receive manual instructions from an operator externally, or may perform stimulation based on internal calculations and programming. The controller 310 is capable of affecting substantially all functions of the IMD 300.

The controller 310 may comprise various components, such as a processor 315, a memory 317, etc. The processor 315 may comprise one or more micro controllers, micro processors, etc., that are capable of performing various executions of software components. The memory 317 may comprise various memory portions where a number of types of data (e.g., internal data, external data instructions, software codes, status data, diagnostic data, etc.) may be stored. The memory 317 may comprise random access memory (RAM) dynamic random access memory (DRAM), electrically erasable programmable read-only memory (EEPROM), flash memory, etc.

The IMD 300 may also comprise a stimulation unit 320. The stimulation unit 320 is capable of generating and delivering stimulation signals to one or more electrodes via leads. The stimulation unit 320 is capable of generating a therapy portion, a ramping-up portion, and a ramping-down portion of the stimulation signal. A number of leads 122, 134, 137 may be coupled to the IMD 300. Therapy may be delivered to the leads 122 by the stimulation unit 320 based upon instructions from the controller 310. The stimulation unit 320 may comprise various circuitry, such as stimulation signal generators, impedance control circuitry to control the impedance "seen" by the leads, and other circuitry that receives instructions relating to the type of stimulation to be performed. The stimulation unit 320 is capable of delivering a controlled current stimulation signal over the leads 122.

The IMD 300 may also comprise a power supply 330. The power supply 330 may comprise a battery, voltage regulators, capacitors, etc., to provide power for the operation of the IMD 300, including delivering the stimulation signal. The power supply 330 comprises a power-source battery that in some embodiments may be rechargeable. In other embodiments, a non-rechargeable battery may be used. The power supply 330 provides power for the operation of the IMD 300, including electronic operations and the stimulation function. The power supply 330, may comprise a lithium/thionyl chloride cell or a lithium/carbon monofluoride cell. Other battery types known in the art of implantable medical devices may also be used.

The IMD 300 also comprises a communication unit 360 capable of facilitating communications between the IMD 300 and various devices. In particular, the communication unit 360 is capable of providing transmission and reception of electronic signals to and from an external unit 370. The external unit 370 may be a device that is capable of programming various modules and stimulation parameters of the IMD 300. In one embodiment, the external unit 370 is a computer system that is capable of executing a data-acquisition program. The external unit 370 may be controlled by a healthcare provider, such as a physician, at a base station in, for example, a doctor's office. The external unit 370 may be a computer, preferably a handheld computer or PDA, but may alternatively comprise any other device that is capable of electronic communications and programming. The external unit 370 may download various parameters and program software into the IMD 300 for programming the operation of the implantable device. The external unit 370 may also receive and upload various status conditions and other data from the IMD 300. The communication unit 360 may be hardware, software, firmware, and/or any combination thereof. Communications between the external unit 370 and the communication unit 360 may occur via a wireless or other type of communication, illustrated generally by line 375 in FIG. 3.

The IMD 300 may also comprise a ramping signal controller 340. The ramping signal controller 340 is capable of providing various definitions of the characteristics of the signal that are to be used to generate the ramping up/down signal portions. The ramping signal controller 340 may provide various signal definitions that may be used by a ramping signal generator 350 to generate the ramping-up/down signals. The ramping signal generator 350 is capable of utilizing various data from the ramping signal controller 340 in order to generate the prescribed ramping-up/down signal portions.

The ramping signal controller 340 may receive various feedback data that may cause it to modify the definition of the characteristics of the ramping up/down signal portions. Data from external sources may be received via the communication unit 360, which may prompt the ramping signal controller 340 to provide particular definitions for the ramping up/down signal portions to the ramping signal generator 350. The ramping signal controller 340 may also be pre-programmed to provide various pre-determined signal definitions to the ramping signal generator 350 for altering the ramping-up/down signal portions.

Further, the ramping signal controller 340 may receive data relating to the efficacy of the therapy delivered by the stimulation signal from an efficacy feedback unit 370. The efficacy feedback unit 370 may comprise various software, hardware, and/or firmware logic that may analyze various indications relating to the efficacy of the therapy being delivered by the IMD 300 and provide an indication of the efficacy to the ramping signal controller 340. For example, if the efficacy seems lower than previous determinations, this information may be send to the ramping signal controller 340, which may react by altering the characteristics of the ramp-up/down signals.

The IMD 300 also comprises a phasic pulse controller 380 that is capable of providing a multi-phasic pulse description to the ramping signal controller 340 in order to implement a multi-phasic ramp-up/down signal. The multi-phasic pulse controller 380 may also comprise a description array 390, which provides an array of data that contains various information relating to implementing a multi-phasic signal. A more detailed description of the multi-phasic pulse controller 380 is provided in FIG. 9 and accompanying description below.

In one embodiment, the multi-phasic pulse description array 390 may reside in the multi-phasic pulse controller 380. In alternative embodiments, the multi-phasic pulse description array 390 may reside in a memory space (e.g., memory unit 365) in the IMD 300. The phasic pulse description array 390 may comprises data for setting various parameters of the pulses of a stimulation signal, such as current amplitude, pulse-width, frequency, pulse polarity, pulse-shape, and the like. In one embodiment, the external unit 370 may download data relating to the multi-phasic pulse description array 390 for implementation of a multi-phasic ramping portion of the stimulation signal.

The ramping signal controller 340, which may comprise a processor that can execute program code, controls the operation of the ramping signal generator 350. The ramping signal generator 350 may generate the current pulses according to parameters defined by the multi-pulse description array 390 and provides these pulses to the ramping signal generator 350 for delivery to the patient via lead assembly 122 and electrode assembly 125. Based upon data from the multi-pulse description array 390, the stimulation unit 350 is capable of implementing multi-phasic controlled current signal outputs for the ramping portion of the stimulation signal. In one embodiment, the various blocks illustrated in FIG. 3 may be a software unit, a firmware unit, a hardware unit, and/or any combination thereof.

Turning now to FIGS. 4A-7C, various examples of a ramp-up signals, in accordance with illustrative embodiments of the present invention are depicted. Although the ramping-up portion of the stimulation signal are exemplified in FIGS. 4A-7C, various ramping-down portions may also be provided in this manner. In some embodiments, the ramping-down portion of the stimulation signal may be symmetrically opposite or complimentary to the ramping-up portion of the signal. Alternatively, variations may exist between the ramping-up and the ramping-down signal portions, in addition to the normal signal amplitude changes. In other words, in some alternative embodiments, full symmetry between the ramping-up and the ramping-down may not exist.

Figure 4B:
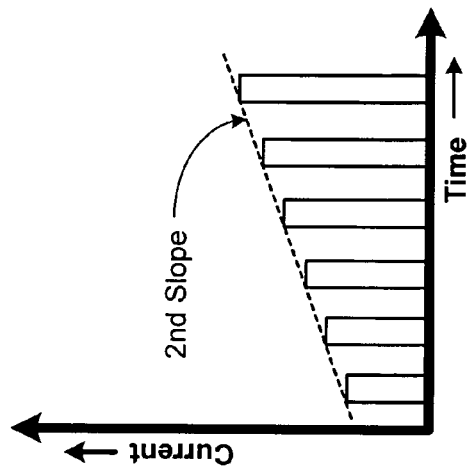
FIGS. 4A-4B illustrate a rate of change modification of various ramp-up signals, in accordance with one illustrative embodiment of the present invention.
Figure 4A:
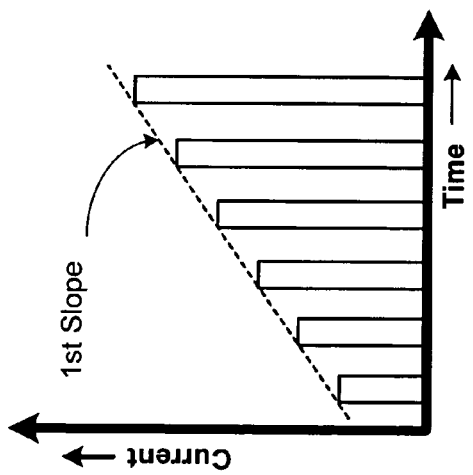

FIG. 4A illustrates a ramp-up signal with a first slope, wherein FIG. 4B illustrates a ramping-up signal with a second slope. Therefore, during one therapy period, the ramping-up portion comprising the first slope may be used, wherein during a second stimulation signal, the ramping-up based on a second slope of the amplitude may be implemented. Therefore, a variation in the rate-of-change of the amplitude of the ramping-up signal may be implemented to achieve the ramping portion variations described herein. Those skilled in the art having benefit of the present disclosure would appreciate that the amplitude slopes illustrated in FIGS. 4A and 4B may also apply to pulse characteristics and frequency characteristics, affecting the ramp-up and/or ramp-down of stimulation signals.

Figure 5B:
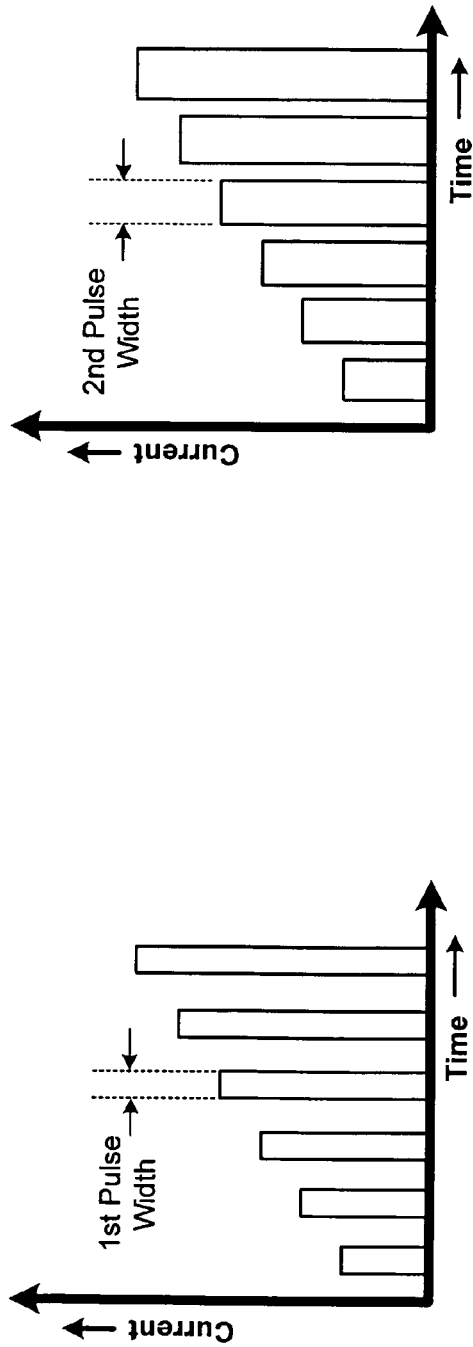
FIGS. 5A-5B illustrate a modification of a pulse width for a ramp-up signal, in accordance with one illustrative embodiment of the present invention.
Figure 5A:
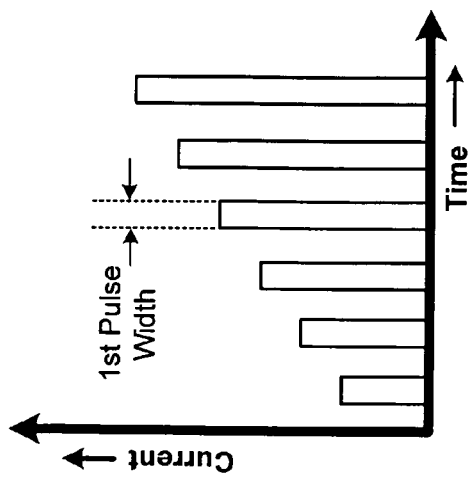

FIG. 5A illustrates a ramping-up of an amplitude with a first pulse width, wherein FIG. 5B illustrates a ramping-up of a signal using a second pulse width. Therefore, the ramping signal controller 340 may implement a pulse width alteration of the ramping-up signal for a first therapy period, and a second pulse width for a second stimulation. Therefore, variations in the pulse-width of the ramping-up signal portions may be implemented to achieve the ramping portion variations described herein.

FIG. 6A illustrates a ramp-up signal portion that has a first duration (e.g., a 3 second duration). In this example, the latter portion of the duration may necessitate a "tapering-off" in the slope of the rate-of-rise. FIG. 6B illustrates a ramp-up signal portion that has a shorter duration (e.g., a 1 second duration). The ramping signal controller 340 may alter the duration of the ramping-up and/or the ramping-down period(s) to provide for increased efficacy of the therapy delivered by the stimulation unit 320. The alteration of the ramping-up and the ramping-down signals portions may call for altering the ramp-up period and the ramp-down period by encroaching into the non-stimulation period and/or encroaching into the stimulation period. Therefore, variations in the duration of the ramping-up signal portions may be implemented to achieve the ramping portion variations described herein.

FIG. 7A illustrates a ramp-up signal portion with a first frequency, wherein FIG. 7B illustrates a ramp-up signal portion with a second frequency. The ramping signal controller 340 may provide for altering the frequency of the ramp-up signal in order to modify the ramp-up and/or the ramp-down signal portions to provide increased efficacy. The ramping-up signal in FIG. 7A comprises a first period ($T_1$), wherein the ramping signal in FIG. 7B comprises a second period ($T_2$). Therefore, the respective frequencies ($F_1=1/T_1$, $F_2=1/T_2$) may be varied for various ramping-up signal portions. Accordingly, variations in the frequency of the ramping-up signal portions may be implemented to achieve the ramping portion variations described herein.

FIG. 7C provides an illustrative, randomized signal portion where various characteristics of the signal may be modified in a random fashion. For example, a random pulse width change may be used, a random amplitude fluctuation may be implemented, a random frequency may be implemented, etc. Additionally, the duration of the ramping-up signal of FIG. 7C may also be randomly modified from one signal to another. Therefore, random modifications of various characteristics from one ramping signal portion to another, or within a signal portion, may be implemented. Accordingly, random variations relating to various characteristics of the ramping signal portions may be implemented to achieve the ramping portion variations described herein.

The modifications of the signal characteristics illustrated in FIGS. 4A-7C may be implemented to change the ramping-up and the ramping-down signal portions to provide for increased efficacy. Although the signals illustrated in FIGS. 4A-7C are described in the context of a ramping-up signal portion, these concepts may also be implemented likewise for a ramp-down signal portion.

Figure 8A:
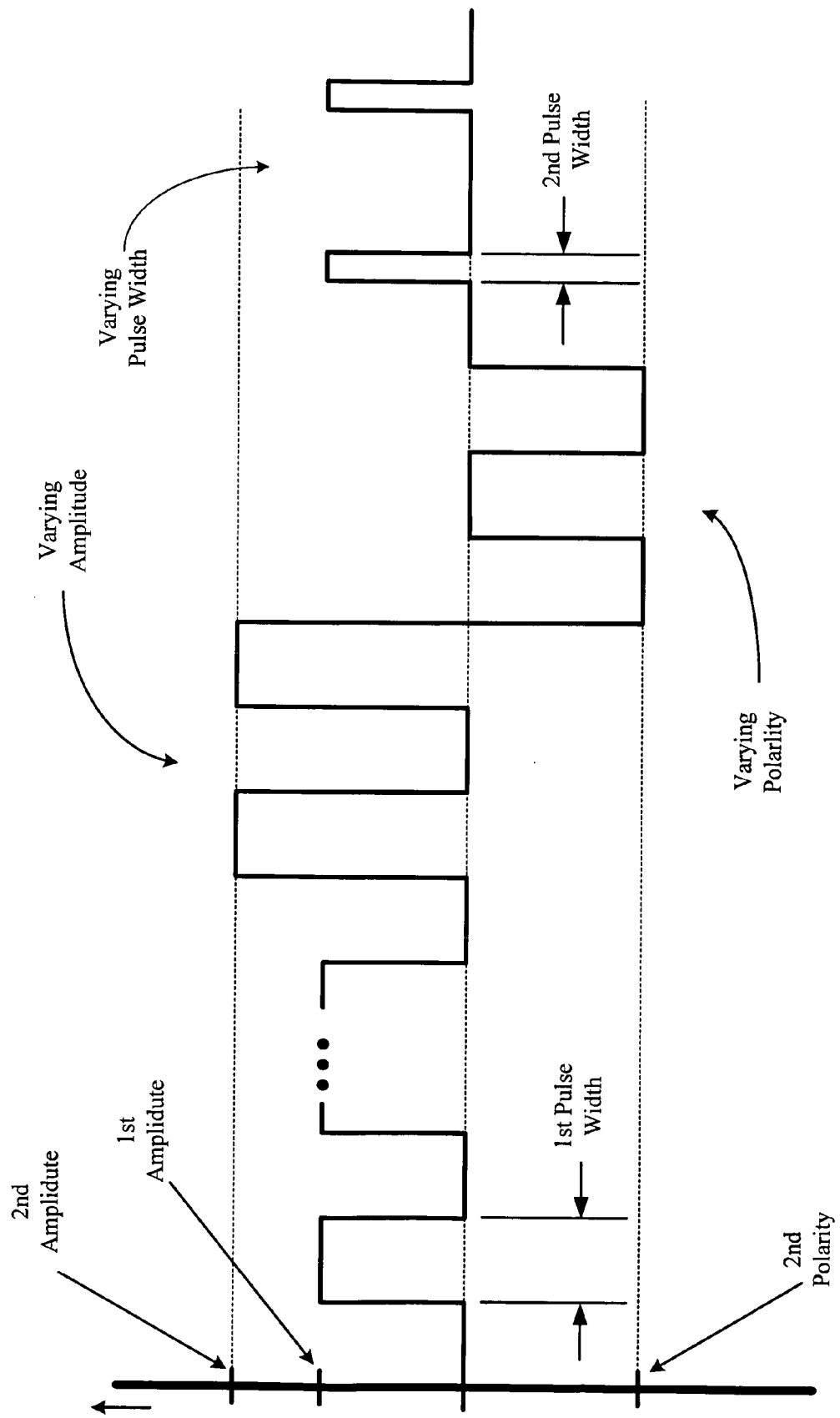

Turning now to FIGS. 8A-8F, exemplary multi-phasic signal waveforms that may be utilized in the ramping signal portions in accordance with illustrative embodiments of the present invention, are provided. The illustrations are presented principally for the sake of clarifying terminology, including the parameters of output signal on-time, off-time, frequency, pulse width, and current. FIG. 8A illustrates an exemplary multi-phasic current signal provided by embodiments of the present invention. Certain parameters may change, however, for particular pulses in a pulse train. In particular, as FIG. 8A illustrates, the pulses of the controlled current signal provided by the IMD 300 may vary in amplitude as illustrated by some pulses having a first amplitude and other pulses having a second amplitude. Furthermore, the polarity of the current signal may vary as indicated by some pulses having a first polarity, indicated by the pulses having a peak above the horizontal zero current line, and other pulses having a second, opposite polarity as indicate by a peak below the zero current line. The signal pulses may also vary in pulse widths as illustrated by the pulses having a first pulse width and a second pulse width, respectively, in FIG. 8A.

Figures 8D, 8E:
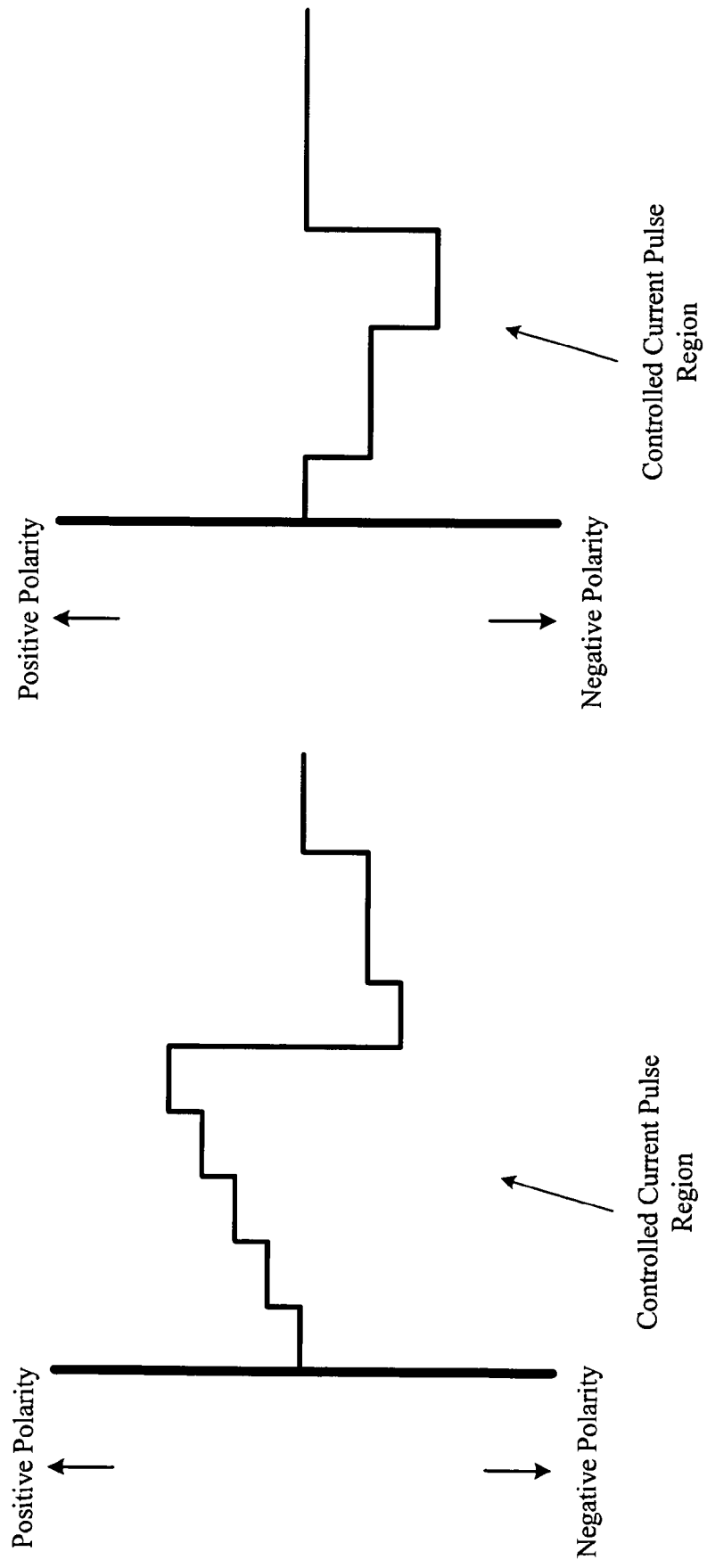

An exemplary multi-phasic stimulation pulse signal provided by the IMD 300 is illustrated in FIG. 8B, where alternating polarity of a pulse signal is illustrated. In one embodiment, the alternating polarity may be employed in conjunction with alternating electrodes for targeting specific tissues. The exemplary stimulation signal illustrated in FIG. 8C depicts a pulse variation in amplitude, pulse width, as well as in polarity. FIG. 8D illustrates an exemplary stimulation signal with a multi-phasic pulse that comprises "stair-step" changes in amplitude, followed by variations in polarity. Therefore, a plurality of phases within a pulse may correspond to a plurality of amplitudes. FIG. 8E illustrates an exemplary stimulation signal with a multi-phasic pulse that provides various phases that correspond to a negative change in amplitude and a change in polarity. A phase of a pulse may take on various shapes and current levels, including a current level of zero Amps. In one embodiment, a phase with zero current may be used as a time delay between two current delivery phases of a pulse.

Figure 8F:
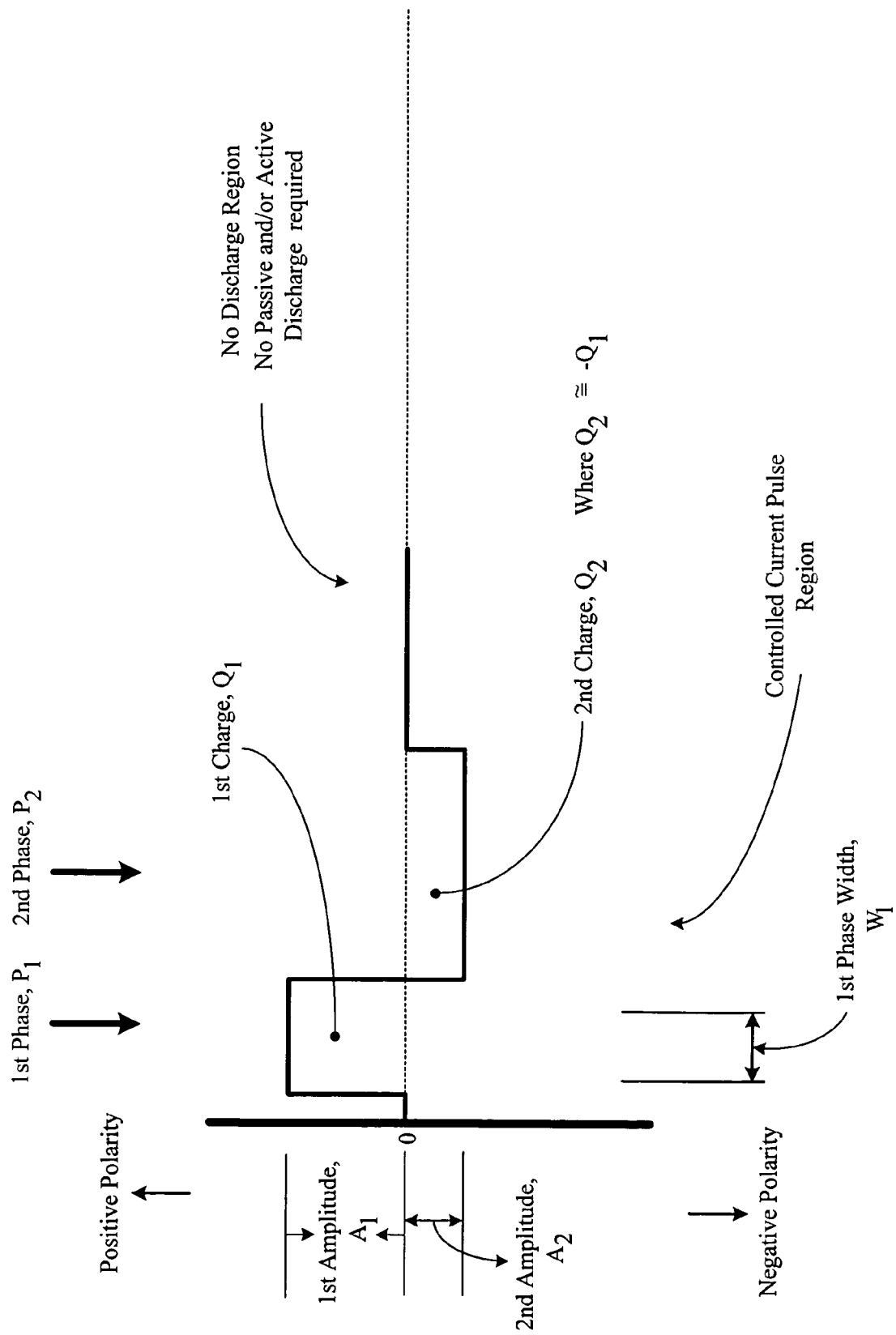

FIG. 8F illustrates a multi-phasic pulse signal and has a first phase that corresponds to a first amplitude relating to a first charge, $Q_1$, and a second phase that corresponds to a second amplitude relating to a second charge, $Q_2$. In the signal illustrated in FIG. 8F, the second charge $Q_2$ is substantially equal to the negative value of the first charge $Q_1$. Therefore, the charges, $Q_1$ and $Q_2$, balance each other, reducing the need for active and/or passive discharging of the charges. Hence, the pulse signal illustrated in FIG. 8F is a charge-balanced, multi-phasic, controlled current pulse signal. Reducing the need for performing active and/or passive discharge may provide various advantages, such as power savings from the reduction of discharging of charge, less circuit requirements, and the like. Various other pulse shapes may be employed in the multi-phasic concepts provided by embodiments of the present invention and remain within the scope and spirit of the present invention.

Figure 9:
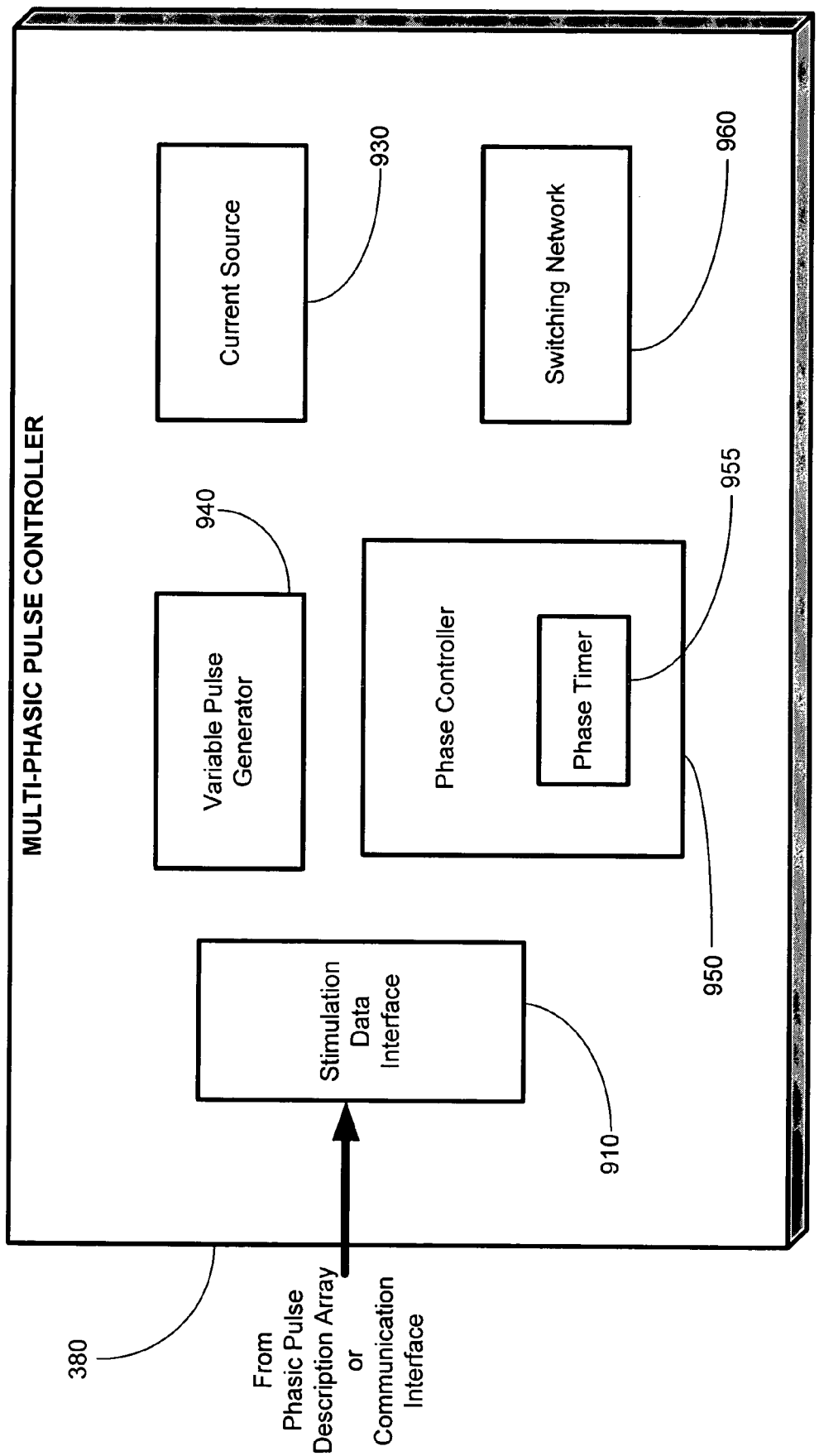
FIG. 9 illustrates a block diagram depiction of a ramping signal generator of FIG. 3, in accordance with one illustrative embodiment of the present invention.

Turning now to FIG. 9, a more detailed block diagram depiction of the multi-phasic pulse controller 380, in accordance with illustrative embodiments of the present invention, is provided. The multi-phasic pulse controller 380 may comprise a stimulation data interface 910 to receive data defining the stimulation pulse. The ramping signal controller 340 is capable of selecting a type of ramping signal definition to be provided by the multi-phasic pulse controller 380. The multi-phasic pulse controller 380 is capable of providing a digital control of the pulses provided by the IMD 300. In an alternative embodiment, the multi-phasic pulse controller 380 is capable of providing an analog control of the pulses provided by the IMD 300.

The stimulation data interface 910 is capable of interfacing with various other portions of the IMD 300. For example, the stimulation data interface 910 may interface with the communication unit 360 (FIG. 3) to receive data from the external unit 370 for determining a particular type of stimulation to be performed. In one embodiment, the stimulation data interface 910 may receive data from the phasic pulse description array 390, which may provide data relating to the type of pulses to be delivered as the stimulation signal. The stimulation data interface 910 may provide data to the stimulation selection unit 920, which then selects a particular type of stimulation to be delivered by the IMD 300.

In one embodiment, the stimulation selection unit 920 may be a hardware unit comprising a processor capable of executing a program code. In an alternative embodiment, the stimulation selection unit 920 may be a software unit, a firmware unit, or a combination of hardware, software, and/or firmware. The stimulation selection unit 920 may receive data from the external unit 370 prompting the unit 920 to select a particular ramping portion pulse regime for delivery by the IMD 300. In one embodiment, the stimulation selection unit 920 may receive a phasic pulse description from the phasic pulse description array 390 that describes a particular type of ramping signal portion with multi-phasic pulses to be delivered by the IMD 300. In an alternative embodiment, the stimulation selection unit 920 may calculate the type of multi-phasic signal pattern to be utilized by the stimulation unit 320 based upon data received from the external unit 370. Therefore, the stimulation data interface 910 receives data relating to the particular type of ramping signal portion to use.

A variable pulse generator 940 may generate a varying electrical pulse shape according to the ramping signal portion defined by the ramping signal controller 340. Based upon the data relating to the type of stimulation to be delivered, the ramping signal controller 340 may provide control signals for selecting a particular type of stimulation signal to be delivered by the IMD 300. The variable pulse generator 940 is capable of generating a number of electrical pulse waveforms for use as the stimulation signal. The pulses may comprise various shapes such as a square wave, a triangular wave, a stepped leading edge and/or trailing edge type pulse, and other pulse shapes. Moreover, a plurality of such shapes may be specified within a single pulse train and/or in sequential pulse trains. Particular shapes may be used for various reasons, such as targeting particular nerve fibers, performing pre-polarization, or hyper-polarization, and the like. The variable pulse generator 940 preferably comprises timing devices and other electronic circuitry for generating the signal pulses.

The multi-phasic pulse controller 380 also comprises a current source 930 to provide a controlled current signal for delivery of stimulation pulses to the patient. The current source 930, in one embodiment, is capable of providing a controlled current even if the impedance across the leads varies (as described below), thereby delivering the stimulation signal from the IMD 300 to a targeted portion of the patient's body.

The multi-phasic pulse controller 380 may also comprise a phase controller 950 for controlling various phases of the stimulation signal. For example, the phase controller 950 may determine the "on" time and the "off" time of each of the pulse phases to be controlled by the multi-phasic pulse controller 380. The multi-phasic pulse controller 380 performs the action as defined by either the phasic pulse description array 390. The phase controller 950 provides a first phase control signal prompting the multi-phasic pulse controller 380 to begin delivering a first type(s) of pulses to the patient. The type of pulse may include various multi-phasic pulses with various shapes, such as the exemplary multi-phasic pulses illustrated in FIGS. 4A-4F. The phase controller 950 may thereafter provide a second phase control signal to terminate delivery of the first type of pulses and begin delivery of a second type of pulses to the patient. The first and second phase control signals may be delivered during a single pulse train or between separate pulse trains. The phase controller 950 may also comprise a phase timer 955, which provides timing control for marking the beginning and end of particular portions of a multi-phasic signal provided by the IMD 300. The phase timer 955 may be any type of timer that is capable of providing timing signals to enable the phase controller 950 to begin and end various phases.

Additionally, the multi-phasic pulse controller 380 may comprise a switching network 960 capable of switching through various polarities and wires. For example, the switching network 960 may switch between various electrodes that may be driven by the IMD 300. Additionally, the switching network 960 may provide a switching mechanism for performing pulse control, as directed by the phase controller 950, to control the pulses provided by the IMD 300. The pulse control may include controlling the various shapes of the pulses, during the duration of the pulse, thereby providing a multi-phasic and/or a non-phasic pulse signal. Thus, using particular sub-modules of the multi-phasic pulse controller 380 (e.g., sub-modules 910-960), the IMD 300 is able to deliver various pulses in various shapes, durations, and polarities, and deliver ramping signal-portions.

Figure 10:
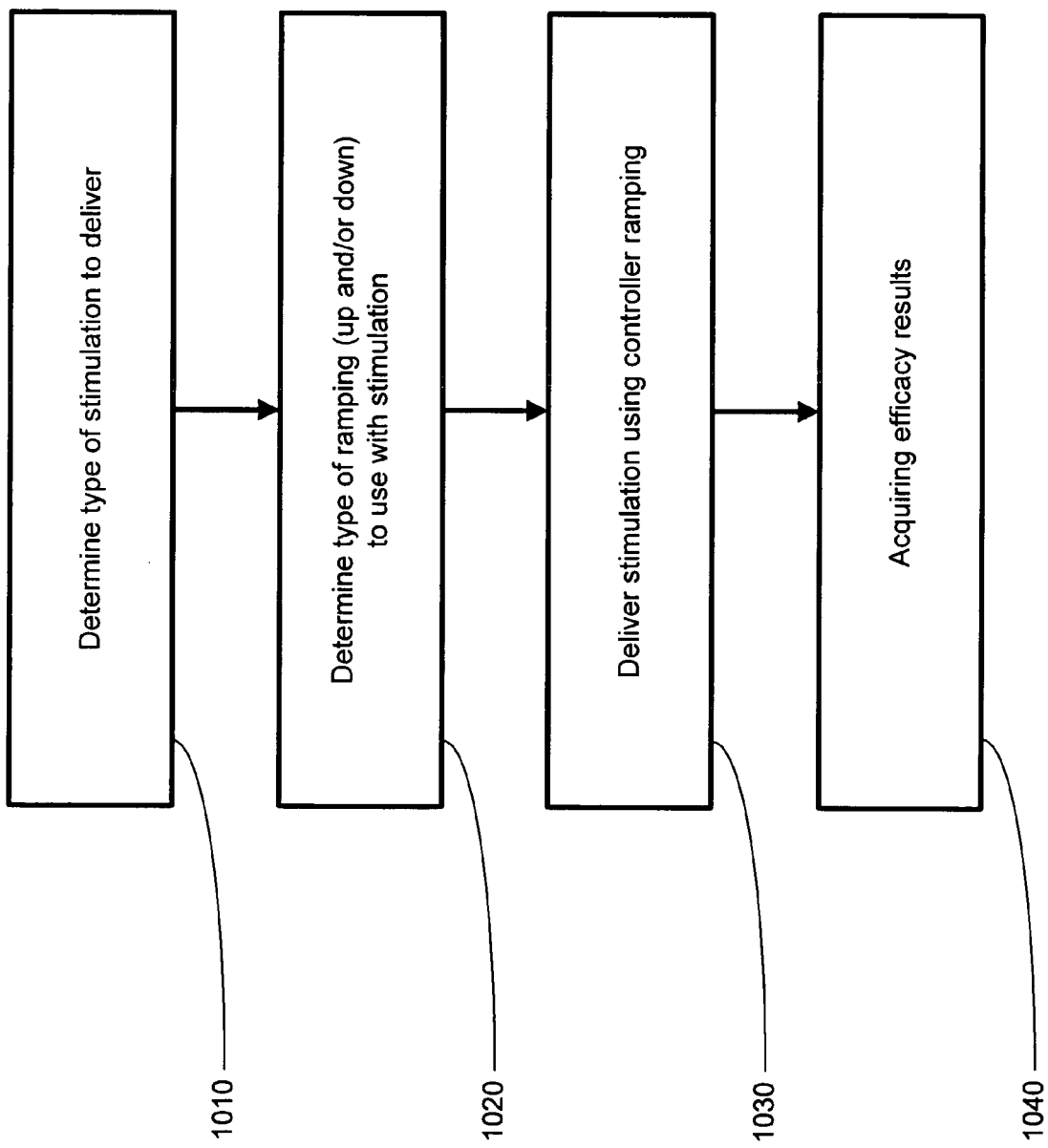
FIG. 10 illustrates a flowchart depiction of the steps of a method, in accordance with one illustrative embodiment of the present invention.

Turning now to FIG. 10, a flowchart depiction of the steps of a method, in accordance with an illustrative embodiment of the present invention is provided. The IMD 300 may make a determination as to the type of stimulation that is to be delivered (block 1010). Determining the type of stimulation may include defining the characteristics of the actual therapy portion, as well as the type of ramping-up/down signals that are to accompany the therapy portion of the stimulation signal. Based upon the type of stimulation to be delivered, the IMD 300 may determine the type of ramping-up/down portions to utilize with the stimulation signal (block 1020). Determining the type of ramping-up/down signal-portions may be based on various factors, such as the type of stimulation signal being applied, commands or instructions from an external source, commands from within the IMD 300, feedback data (e.g., efficacy feedback data relating to prior stimulation), etc. A more detailed description of the step of determining the type of ramping signal to apply is provided in FIG. 11 and accompanying description below.

Upon determining the type of ramping signal to apply, the IMD 300 may deliver the stimulation signal using the determined/calculated or pre-programmed ramping portion control methods described above (block 1030). Therefore, a stimulation therapy period is implemented using the controlled ramp-up period and ramp-down periods to accompany the therapy period, as illustrated in FIG. 2. Upon delivering the stimulation signal, the IMD 300 may acquire efficacy results based on the supplied stimulation (block 1040). These results may be an immediate feedback or a gradual collection of data and analysis that may provide the efficacy indications based on the current stimulation periods in the ramp-up and ramp-down periods being used. Upon acquisition of the efficacy results, various feedback may be provided to further adjust the ramping signals.

Figure 11:
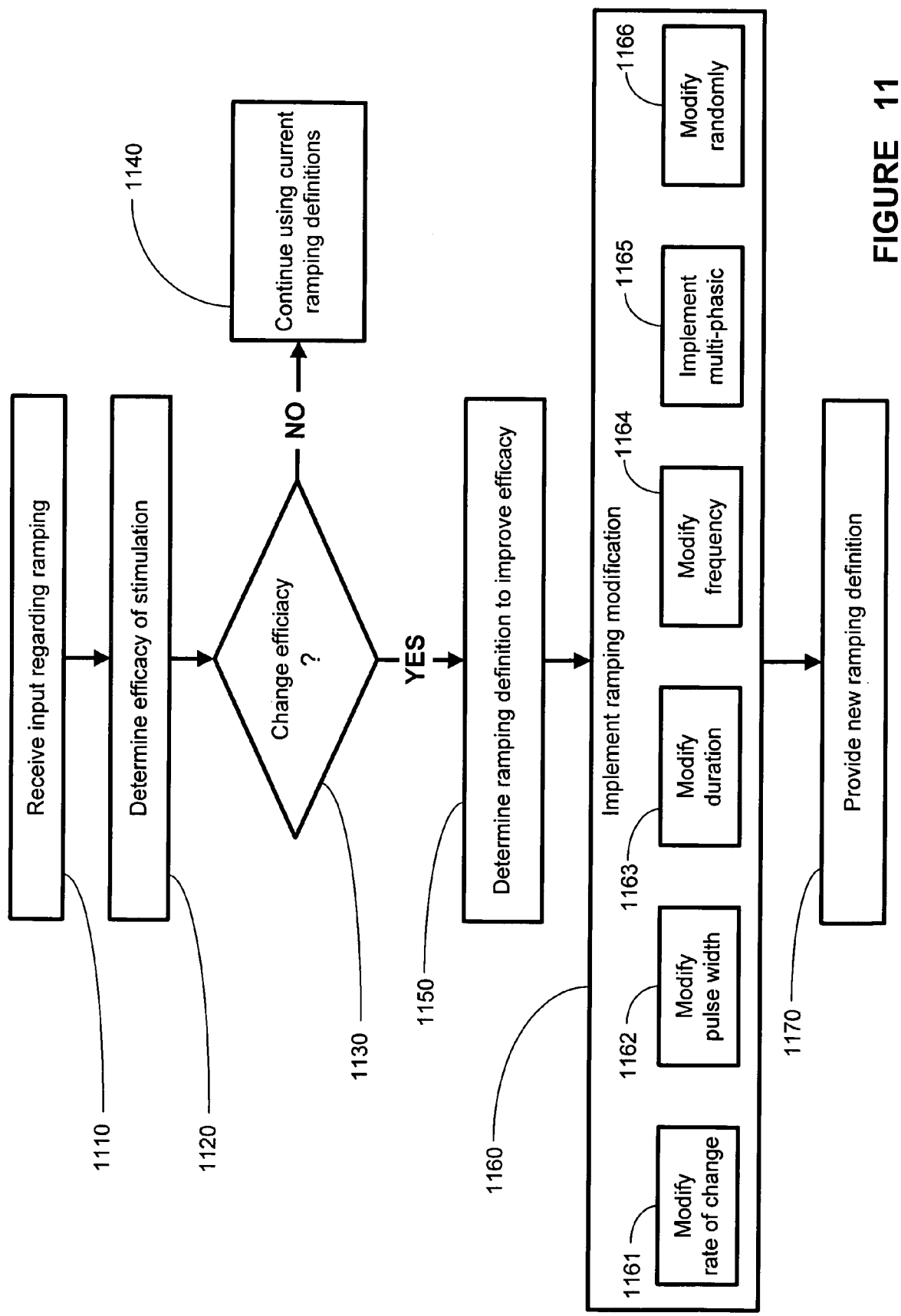
FIG. 11 illustrates a flowchart depiction of the steps for performing determining the type of ramping to be utilized in accordance with one illustrative embodiment of the present invention.

Turning now to FIG. 11, a more detailed flowchart depiction of the steps for determining the type of ramping signal portion to implement, as indicated in block 1020 of FIG. 10, is provided. The IMD 300 may receive input regarding the type of ramping signal to apply (block 1110). This input may be based on external input received by the communication unit 360. For example, a physician may analyze a patient's progress and may determine that an alteration of the ramping-up/down signals may be desirable to improve efficacy of the therapy. Other inputs, such as an input from the patient, could be received from the external device 370 via the communication unit 360.

Based upon the input, and/or based upon independent determination, the IMD 300 may estimate the efficacy of the stimulation (block 1120). This determination may be based on data relating to recent stimulations, or long-term data that may be indicative of the efficacy of the long-term stimulation therapy. The IMD 300 may then make a determination whether to change the efficacy based upon the data received (block 1130).

If the IMD 300 determines that the efficacy is not to be changed and that the efficacy is relatively satisfactory, the IMD 300 may continue using the current ramping definitions (block 1140). However, if the IMD 300 determines that the efficacy is to be changed, or input regarding the ramping signals indicates that the current ramping is to be changed, and/or pre-programmed indications specify that the ramping characteristic(s) are to be changed, a modification of the ramping definition for improving efficacy may be determined (block 1150). Various algorithms and physiological data may be used to determine the type of ramping definition to be provided.

Based on determining ramping definition, the IMD 300 may implement the ramping modification (block 1160). This implementation may include various ramping signal modifications, such as modifying the rate of change (block 1160), modifying the pulse width (block 1162), modifying the duration of the ramping period (block 1163), modifying the frequency of the ramping signal (block 1164), implementing a multi-phasic ramping signal (block 1165), and/or implementing a randomized modification of one or more ramping signal-portion characteristics described above (block 1166). One or more of the characteristics described above may be modified for subsequent ramping-up/down signal portions. The new ramping definitions are then provided to the ramping signal generator 350 to implement the ramping signal-portion changes (block 1170). Based upon the new ramping definitions, a modified ramping-up period and/or a ramping-down period may be implemented when providing the stimulation signal therapy.

Utilizing embodiments of the present invention, a modification to the ramping-up/down signals may be implemented. Various benefits may be realized utilizing these techniques, such as improved efficacy, reduced therapy periods, etc. Therefore, a reduction in neural conditioning may be achieved while maintaining desirable therapeutical efficacy when delivering therapeutic stimulation signals.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. An implantable medical device for providing an electrical neurostimulation therapy to a patient, the implantable medical device comprising:

a ramping signal controller configured to generate via a ramping signal generator a first electrical signal comprising a first ramping portion which is based on a first parameter including at least one of an amplitude, a rate of change of the amplitude, a time period of the rate of change of the amplitude, a pulse width, a rate of change of the pulse width, a time period of a rate of change of the pulse width, a frequency, a rate of change of the frequency, a time period of a rate of change of the frequency, and a duration of a time period of the first ramping portion, the first parameter having a first value;

the first electrical signal being applied to a target location of the patient's body;

the ramping signal controller being configured to determine via an efficacy feedback unit a second value for the first parameter for a second electrical signal based on a neural conditioning value, the second value being different than the first value and the second value having a randomized portion;

the ramping signal controller being further configured to generate via the ramping signal generator the second electrical signal comprising a second ramping portion based on the second value, wherein the second value is chosen by the ramping signal controller to reduce neural conditioning; and wherein the second electrical signal is applied to the target location of the patient's body.

2. The implantable medical device of claim 1, wherein the first electrical signal comprising the first ramping portion includes at least one of a ramping-up portion having the first parameter and a ramping-down having the first parameter.

3. The implantable medical device of claim 2, wherein the ramping portion comprises at least one of the ramping-up portion having the second value and the ramping-down portion having the second value.

4. The implantable medical device of claim 1, wherein the second electrical signal is based on the second value that differs randomly from the first value.

5. The implantable medical device of claim 1, wherein the second electrical signal is utilized to provide a multi-phasic signal for the ramping portion.

6. The implantable medical device of claim 1, wherein the second electrical signal is based on at least one of an external command, an internal programmed command, and a feedback indication.

7. The implantable medical device of claim 1, wherein the second electrical signal is based on data relating to an efficacy associated with the stimulation.

8. A method for providing an electrical neurostimulation therapy to a patient using an implantable medical device (IMD), comprising:

generating a first electrical signal comprising a first ramping portion which is based on a first parameter including at least one of an amplitude, a time period of a rate of change of the amplitude, a pulse width, a rate of change of the pulse width, a time period of the rate of change of the pulse width, a frequency, a rate of change of the frequency, a time period of a rate of change of the frequency, and a duration of a time period of the first ramping portion, the first parameter having a first value;

applying the first electrical signal to a target location of the patient's body;

determining a second value for the first parameter for a second electrical signal based on a neural conditioning value, the second value being different than the first value and the second value having a randomized portion;

generating the second electrical signal comprising a second ramping portion based on the second value, wherein the second value differs randomly from the first value and is chosen by the IMD to reduce neural conditioning; and applying the second electrical signal to the target location of the patient's body.

* * * * *